(12) United States Patent
Müsken et al.

(10) Patent No.: US 10,179,928 B2
(45) Date of Patent: Jan. 15, 2019

(54) METHODS AND TESTS FOR SCREENING BACTERIAL BIOFILMS

(75) Inventors: Mathias Müsken, Braunschweig (DE); Susanne Häußler, Salzgitter (DE)

(73) Assignee: Helmholtz-Zentrum fuer Infektionsforschung GmbH, Braunschweig (DE)

( * ) Notice: Subject to any disclaimer, the term of this patent is extended or adjusted under 35 U.S.C. 154(b) by 0 days.

(21) Appl. No.: 13/387,228

(22) PCT Filed: Jul. 30, 2010

(86) PCT No.: PCT/EP2010/004670
§ 371 (c)(1),
(2), (4) Date: Jan. 26, 2012

(87) PCT Pub. No.: WO2011/012311
PCT Pub. Date: Feb. 3, 2011

(65) Prior Publication Data
US 2012/0122729 A1    May 17, 2012

Related U.S. Application Data

(60) Provisional application No. 61/229,916, filed on Jul. 30, 2009.

(51) Int. Cl.
*C12Q 1/18* (2006.01)
*C12Q 1/04* (2006.01)

(52) U.S. Cl.
CPC ............... *C12Q 1/18* (2013.01); *C12Q 1/04* (2013.01); *G01N 2800/52* (2013.01)

(58) Field of Classification Search
CPC . C12M 1/267; C12Q 1/02; C12Q 1/04; C12Q 1/18
See application file for complete search history.

(56) References Cited

U.S. PATENT DOCUMENTS

| | | | |
|---|---|---|---|
| 5,863,792 A * | 1/1999 | Tyndorf et al. | 435/297.5 |
| 2008/0038769 A1 * | 2/2008 | Bernardi et al. | 435/29 |
| 2008/0318269 A1 * | 12/2008 | Olson et al. | 435/39 |
| 2010/0248995 A1 * | 9/2010 | Kensy et al. | 506/39 |
| 2011/0281921 A1 * | 11/2011 | Srebnik | A01N 37/32 514/369 |

FOREIGN PATENT DOCUMENTS

DE    10 2008 008 256 A1 *    4/2009    ............ B01J 19/24

OTHER PUBLICATIONS

Machine Translation of DE 10 2008 008 256 A1. Apr. 9, 2009.*

* cited by examiner

*Primary Examiner* — Nancy J Leith
(74) *Attorney, Agent, or Firm* — Whitham & Cook, P.C.

(57) ABSTRACT

In a first aspect, the present invention relates to a method for screening bacteria on their susceptibility against candidate compounds. In a further aspect, the present invention relates to a method for screening the antibiotic efficacy of candidate compounds suppose to have an antibiotic activity on bacteria. Moreover, the present invention relates to a method for forming a bacterial biofilm on a support, a system allowing in vitro and in vivo evaluation of biofilms formed by bacteria as well as methods for the stratification of the treatment regimen against bacterial infections.

10 Claims, 9 Drawing Sheets

METHODS AND TESTS FOR SCREENING BACTERIAL BIOFILMS

CROSS-REFERENCE TO RELATED APPLICATIONS

This application is a national stage filing under Rule 371 from international application PCT/EP2010/004670 filed Jul. 30, 2010 which claimed priority to U.S. provisional 61/229,916 filed Jul. 30, 2009.

In a first aspect, the present invention relates to a method for screening bacteria on their susceptibility against candidate compounds. In a further aspect, the present invention relates to a method for screening the antibiotic efficacy of candidate compounds supposed to have an antibiotic activity on bacteria. Moreover, the present invention relates to a method for forming a bacterial biofilm on a support, a system allowing in vitro and in vivo evaluation of biofilms formed by bacteria as well as methods for the stratification of the treatment regimen against bacterial infections.

PRIOR ART

Clinicians who deal with device-related and other chronic bacterial infections increasingly face a new category of infectious diseases that differs radically from the acute epidemic bacterial infections. These diseases are much less aggressive than acute infections, they often persist for months or years, and they progress through periods of latency that alternate with periods of acute exacerbation. However, although traditional antibiotic therapy gives some relief during acute exacerbations, these antibiotics fail to resolve the bacterial infections[1].

Chronic bacterial infections with *Pseudomonas aeruginosa* have an exclusive role in the pulmonary infection of cystic fibrosis (CF) patients. The majority of the CF patients acquire *P. aeruginosa* and in these patients chronic lung infection, repeated exacerbations, and progressive deterioration in lung function remain a major cause of morbidity and mortality. In the chronically infected CF lung, *P. aeruginosa* adopts a biofilm mode of growth with the formation of structured microbial communities that grow within microcolonies embedded in an extracellular matrix and it has been shown that with the formation of bacterial biofilms it becomes impossible to eradicate the infection[2]. Biofilm bacteria are much more resistant to antibiotic treatment as well as to the host immune response[3]. The formation of bacterial biofilms profoundly influences the biological activities of the constituting bacteria in a way that is not easily predicted on the basis of our current knowledge[4].

Despite the evidence that *P. aeruginosa* grows in the airway of CF patients within microcolonies, conventional clinical susceptibility testing involves the culture of planktonically grown bacteria that have been recovered from the respiratory tract of CF patients. Consequently, antibiotic therapy is directed by these susceptibility test results to treat symptomatic CF patients with chronic infections. However, it seems reasonable that the antibiotic susceptibilities of planktonic populations as determined by MIC methodologies do not necessarily reflect the actual resistance profile in vivo[5].

One may argue that the strategies of susceptibility testing should account for differences in growth behavior within biofilms, where the bacteria grow slowly and densely packed in an anaerobic or microaerophilic environment. Previous studies comparing the antibiotic resistance profile of biofilm versus planktonic grown *P. aeruginosa* revealed that there is obviously not a single agent or combination of agents that predominates the biofilm susceptibility profile of CF isolates and others have shown that patients treated with biofilm-effective therapy had improved clinical outcomes[6]. This implicates that there seems to be a need for an individualized biofilm susceptibility testing in the clinical setting. Nevertheless, even if antimicrobial biofilm resistance would be strain specific, it is indispensable to clearly show that biofilm susceptibility testing results in sufficiently different treatment regimes and that there is a benefit of these treatment regimes for the CF patients in a prospective clinical trial. However, the major problem faced in the evaluation of the benefit of alternative antibiotic treatment has been the lack of a suitable assay which could provide the clinicians with an antibiotic resistance profile of biofilm grown bacteria. The use of a standardized and reliable high-throughput system to monitor biofilm growth under the addition of various antibiotics may overcome this hindrance. Biofilms are surface-attached microbial communities embedded in a self-produced extracellular polymeric matrix. Biofilms contribute markedly to the persistence of pathogens on medical devices or industrial equipment, leading to critical problems in terms of public health and a potentially major economic impact.

In 1999 a 96-well based assay to monitor biofilm formation followed by quantitative microbiology was established in the H. Ceri lab and since then was widely used to test antimicrobial resistance profiles of biofilm grown clinical isolates in several bacterial pathogens[7]. However, this test system is very material and time consuming and hardly applicable for antimicrobial resistance testing in routine diagnostics. Other alternative methods to quantify microbial biofilms have been tested for various organisms. One of these alternative methods for the testing of drug-effects on biofilm cells is the colorimetric determination of metabolic activity following drug exposure, e.g. Pierce et al.[8], which requires less post-processing of the samples and correlates with cell viability as opposed e.g. to crystal violet staining of the bacterial biofilm mass. However, marked inter-strain differences in the ability to metabolize the substrate have been described and the bacterial metabolism per se is affected in the various phases of biofilm development which may impact on the test outcome. Another alternative is the determination of viability via different combinations of fluorescent dyes as an indicator of live and dead bacteria[9,10]. Applied in various systems for antibiotic testing of biofilms especially the commercial available BacLight kit—or one of its compartments Syto9 or propidium iodide—was broadly used for viability determination[11].

Viability staining has become a powerful tool, particularly in combination with confocal laser scanning microscopy (CLSM). The use of CLSM of biofilms formed in flow-chamber experimental systems and the use of image analysis programs have provided a detailed knowledge about biofilms under controlled and reproducible conditions. Furthermore, this technique allows the visualization of biofilm subpopulations affected by antimicrobial agents or bacteriophage activity. The major drawback, however, is that only relatively few equivalent biofilms can be produced at the same time in these systems and hence this method is too time and labor intensive for large-scale approaches[12].

SHORT DESCRIPTION OF THE PRESENT INVENTION

Here, it is demonstrated that BacLight viability staining in combination with automated CLSM is a highly effective and rapid method to monitor the efficiency of various antibiotics and at the same time allows conclusions to be drawn about the constitution of the bacterial population as presented in example 1. Moreover, a reliable method is described that provides detailed structure-function information on *P. aeruginosa* grown under biofilm conditions in e.g. a 96-well plate format, which has been successfully used within a genetic screen for *P. aeruginosa* mutants, affected in the formation of biofilms as shown in the example 2. Microscopic data and 3D visualizations thereby give details on the nature of the biofilm in respect to various physical parameters such as cell mass, cell density, extracellular matrix and three-dimensional structure of the bacteria within the biofilms.

Due to the high-throughput scale, the system according to the present invention is suitable for rapid antibiotic testing of biofilms and offers a simple and flexible method for the identification of multiple parameters and factors influencing biofilm formation, or the analysis of strain- or mutant-specific biofilm phenotypes.

Furthermore, it is demonstrated that the methods according to the present invention are suitable to test samples containing multiple types of bacteria as they can, for example, be found in sputum of CF patients. Hence, prior isolation of single species from the bulk sample is not required.

DETAILED DESCRIPTION OF THE PRESENT INVENTION

In a first aspect, the present invention relates to a method for screening bacteria on their susceptibility against candidate compounds comprising the steps of:
  a) forming of a biofilm of said bacteria on a planar support whereby said planar support is adapted for microscopy;
  b) incubating the formed biofilm of bacteria of step a) with the candidate compounds to be tested;
  c) staining the bacterial biofilm of step b) with a marker allowing detection of said bacteria, in particular, allowing differentiation between live bacteria and dead bacteria;
  d) evaluating the effect of the candidate compounds on the bacteria present in the biofilm based on the staining pattern using a microscope, optionally, having a processing unit;
  e) determining the susceptibility of the bacteria tested against the candidate compounds based on the staining pattern of the bacteria.

In a further aspect, the present invention relates to a method for screening the antimicrobial, in particular, the antibiotic efficacy of candidate compounds supposed to have an antimicrobial, in particular, an antibiotic activity on bacteria comprising the steps of:
  a) forming of a biofilm of said bacteria on a planar support whereby said planar support is adapted for microscopy;
  b) incubating the bacterial biofilm obtained in step a) with the candidate compounds supposed to have an antimicrobial, in particular, an antibiotic activity;
  c) staining the treated bacterial biofilm of step b) with a marker allowing detection of said bacteria, in particular, allowing differentiation between living bacteria and death bacteria;
  d) evaluating the effect of the candidate compounds on the bacteria present in the biofilm based on the staining pattern using a microscope and, optionally, a processing unit;
  e) determining the susceptibility of the bacterial strain against the candidate compounds for an antimicrobial, in particular, an antibiotic activity against said bacterial strain.

Moreover, the present invention relates to a method for forming a biofilm of bacteria on a support comprising the step of cultivating the bacteria on a support to allow biofilm formation whereby the cultivation takes place in a rich cultivation medium and cultivation is effected in containers covered with an air-permeable cover to prevent an oxygen gradient from the outer to the inner zone of said container covered with a cover like a lid or foil.

In this connection, the term "air-permeable cover" refers to a cover which is substantially air-permeable for gaseous compounds, in particular, air, like $O_2$ in its entirety. That is, the cover allows a gaseous exchange substantially over the whole area of the cover. This is in contrast to conventionally used cover of microtitre plates which are hardcover made of plastic where a gaseous exchange is possible at the boarder area, namely the gap between cover and plate. The use of said air-permeable cover allows minimizing gaseous gradient, in particular, oxygen gradient, in the microenvironment of said plate.

The present inventors were successful in establishing a bacterial biofilm on a support which allow direct evaluation of said biofilm in situ using a microscope, in particular, a CLSM.

According to the present invention, the term "planar support is adapted for microscopy" refers to a support which allows observing the biofilm formed on said planar support directly with the microscope. This requires a sufficiently formed support. Namely, the support must be formed sufficiently thin to allow the use of a microscope. Furthermore, the thickness over the area observed must be substantially identical to allow a sufficient accurate analysis.

Moreover, the biofilm of the bacteria is formed on the planar surface of said support. That is, the biofilm is attached to the planar surface of the support.

The term "candidate compounds" refers to chemical or biological entities known in the art. For example, the candidate compounds include small molecules present in libraries available for high throughput screening.

The candidate compounds may be known compounds having an antibiotic activity. In this context, the term "candidate compounds supposed to have antimicrobial activity" refers to compounds useful for treating infections caused by microorganisms; the term "candidate compounds supposed to have an antibiotic activity on bacteria" refers to compounds which are useful for inhibiting bacterial growth and/or killing bacteria e.g. already described in the art. The candidate compounds may have known antimicrobial/antibiotic activity or may be a compound to be tested for said activity.

The marker molecule allowing differentiation between living bacteria and death bacteria is preferably the Syto9 and propidium iodide (PI) system, available for example as LIVE/DEAD® BacLight™ bacterial viability kit from Invitrogen/Molecular Probes.

Preferably, the support according to the present invention is part of a 96-well plate or a 384-well plate. In another preferred embodiment, the cultivation of the bacteria takes place in a rich medium promoting fast growth of bacteria. Thus, the biofilm is formed on the bottom of the wells. The LB medium was the media of choice, however, other rich media like brain-heart infusion (BHI) medium or Mueller-Hinton (MH) medium are also suitable depending on the type of bacteria forming the biofilm. Thus, preferably, cultivation takes place in containers covered with an air-permeable cover. The present inventors found that an oxygen gradient from outside to inside the container covered with a sealing cover negatively influence the formation of the biofilm.

The method is preferably performed by using a laser scanning microscope, preferably having an automated processing unit. Said processing unit allows determining and evaluating the effect of the candidate compounds on the bacteria present in the biofilm.

The method and system as claimed herein are particularly useful for high throughput screening of candidate compounds. Typically, the evaluation and determination of susceptibility includes comparing the test sample of the bacterial biofilm incubated with the candidate compound with a reference sample, in particular, a control not incubated with the candidate compound or with a compound known to have an effect on the bacterial biofilm.

In a further aspect, the present invention relates to a method for screening bacterial mutants having altered biofilm development comprising the steps of:
 a) cultivating the bacteria on a planar support whereby said support is adapted for microscopy;
 b) staining the bacterial biofilm formed in step a) with a marker allowing detection of bacteria;
 c) evaluating the biofilm formed in step a) based on the staining pattern using microscopy and, optionally, a processing unit;
 d) determining bacterial mutants having altered biofilm formation ability when comparing the ability of biofilm formation with a non-mutated reference bacteria strain.

An example thereof is described below. Further, the present invention provides a method for the stratification of the treatment regimen against bacterial infections comprising the step of determining the antimicrobial, in particular, the antibiotic efficacy of compounds having antimicrobial, in particular, antibiotic activity on bacteria derived from subjects afflicted with bacterial infections. Thus, applying the method according to the present invention allows determining the susceptibility profile of the tested isolate and hence, identify, optimize (change or adapt) treatment regimen for individuals being infected with bacterial infection.

Moreover, the present invention relates to a system for the in vitro and in vivo evaluation of biofilms formed by bacteria comprising containers for cultivation of bacteria allowing formation of biofilms whereby said containers comprise a planar area adapted for microscopy; a cover for said container which is an air-permeable cover; a laser-scanning microscope, optionally, having a processing unit. Preferably, the system includes marker allowing differentiation between live and death bacterial cells and cell system is adapted for high throughput screening. Of course other cell- or biofilm-specific marker can be used as well.

Additionally, the methods and systems according to the present invention can be used for susceptibility testing of mixed bacterial communities. That is, the bacteria for forming the biofilm may be provided in form of isolated bacterial strains or may be provided as a mixed bacterial community. In case of a mixed bacterial community of multiple species, a biofilm of said multispecies may be formed which can be analysed for antimicrobial, in particular, antibiotic susceptibility. The bacteria may be derived or isolated from biological samples. The biological samples may be used for forming the bacterial film directly or may be used in diluted forms. The biological sample is preferably a sample obtained from body fluid, like sputum, saliva, blood, or a tissue derived biological sample obtained by extraction, isolation or purification from a tissue or body fluid source.

Particularly preferred, the biological sample is sputum or saliva. For example, the sputum obtained from an individual may be used in diluted or undiluted form. Dilution may be effected with physiological acceptable liquids like saline or suitable culture medium, e.g. a rich culture medium. Optionally, the bacteria used for forming the biofilm are isolated in advance according to generally known methods.

Hence, the present invention provides methods and systems for testing the capability of bacterial strains, e.g. of *P. aeruginosa* strains and mutants derived there from to form biofilms or to test the impact of antimicrobial, in particular, antibiotic compounds on bacterial biofilms. Thus, in addition to susceptibility testing and screening for a biofilm effective mutants within large mutant libraries the method according to the present invention as well as the systems are provided herein can be applied to screen compound libraries to identify new potential anti-biofilm drugs. Moreover, the method according to the present invention is applicable for multispecies biofilms. In particular, the method according to the present invention is useful for determining susceptibility of the respective bacteria to a therapeutic regimen including administration of antibiotics.

In particular, the methods according to the present invention allow the standardisation of the assessment of clinical samples, e.g. biological samples obtained from individuals affected with a bacterial infection, for determining antibiotic efficiency on biofilm formation. In particular, standardised determination of antibiotic efficiency on *P. aeruginosa* biofilms is possible as demonstrated herein.

In a preferred embodiment, the present invention relates to a system for the evaluation of biofilms formed by bacteria comprising the containers for cultivation of bacteria allowing formation of biofilms whereby said containers comprise a planar area adapted for microscopy; a cover for said container which is an air-permeable cover; a laser scanning microscope, optionally, having a processing unit. The air-permeable cover is a cover formed from a material which allows exchange of the air over the entire cross sections. That is, the air-permeable cover is a cover allowing gas penetration substantially in the same amount over the whole area.

The use of this air-permeable cover allows providing a microenvironment where oxygen gradient from the outer to the inner zone of said container covered by the cover are reduced to a minimum. This is particularly true for a container which is a well plate, in particular, a multiple well plate, like a 96 well plate, a 384 well plate and the like.

The invention is illustrated further with the following examples without being limited thereto.

EXAMPLES

Experimental Design

The *P. aeruginosa* PA14 strain was used initially to optimize parameters of biofilm formation in the 96-well-plate format. The PA14 strain is fully sequenced and an ordered comprehensive mutant library is available to the scientific community[13]. A prerequisite for the microscopic evaluation of *P. aeruginosa* biofilms is the formation of robust biofilms at the bottom of the microtitre plate. Biofilm formation is critically influenced by medium conditions, culture time, bacterial inoculum, oxygenation, viability staining and image processing. A further optimization step was the use of air permeable cover foils to prevent an oxygen gradient from the outer to the inner wells, thus the use of air-permeable cover is preferred. After standardizing the pivotal conditions, the procedure was used to test PA14 and five clinical CF isolates for their antimicrobial susceptibility profiles under biofilm growth conditions. Clinical isolates were recovered from the respiratory tracts of chronically infected people with CF at the Hannover Medical School and differed according to morphology and resistance profile. The MICs were determined by the use of the semi-automated Vitek2 system (Biomerieux). All strains were stored longer term in glycerol stocks at −70° C. and fresh cultures were routinely prepared in Luria Bertani (LB) medium or on LB agar plates.

Materials
Reagents
  LB medium (7.5 g NaCl (e.g. Roth, cat. no. 3957.1), 5 g Bacto™ Yeast-extract (e.g. Becton Dickinson, cat. no. 212750), 10 g Bacto™ Tryptone (e.g. Becton Dickinson, cat. no. 211705) in 1 liter distilled water)
  Bacto™ Agar (e.g. Becton Dickinson, cat. no. 214010)
  Sodium-chloride solution (0.9% NaCl in distilled water (wt/vol))
  LIVE/DEAD® BacLight™ Bacterial Viability Kit (Molecular Probes/Invitrogen, cat. no. L-7012)
  Dimethylsulfoxid (DMSO) (e.g. Riedel-de Haen, cat. no. 60153)
  Glycerol, >86% p.a. (e.g. Roth, cat. no. 4043.3))
  Antibiotics: tobramycin sulfate salt (Sigma, T1783), Ciprobay 100 (Bayer Vital), ceftazidime hydrate (Sigma, C3809), Meronem (AstraZeneca), Colistin sulfate (bigma, C4461)
  distilled water ($dH_2O$)
  isopropanol (e.g. Roth, cat. no. 6752.1)
Equipment
  Incubator at 37° C. with a water reservoir for humid atmosphere
  Orbital shaker (e.g. Infosors-HT)
  Plastic-box (~22 cm×17 cm×6 cm) for a humid atmosphere in the orbital shaker
  Autoclave
  Sterile half area 96-well μClear® microplate (Greiner Bio-one, cat. no. 675090)
  PP-testtubes, 15 ml (e.g. Greiner Bio-one, cat. no. 188271)
  Safeseal tube, 1.5 ml (e.g. Sarstedt, cat. no. 72.706)
  Class II biological safety cabinet (e.g. Baker Company)
  Vortex mixer
  Inverse confocal laser scanning microscope (e.g. automated: Opera-system, Perkin-Elmer—Cellular Technologies or manual: FluoView FV1000, Olympus)
  Air-permeable BREATHseal cover foil (Greiner Bio-one, cat. no. 676051)
  Multichannel pipette (e.g. Transferpette, Brand)/normal pipettes (e.g. Gilson)
  Spectrophotometer capable of reading absorbance at 600 nm
  Sterilizing Filter (0.22-μm pore size) (e.g. Pall Corporation, cat. no. 4652)
  10 ml Syringe (e.g. Becton Dickinson, cat. no. 2012-04)
  75 ml reservoir+lid, autoclavable, for multichannel pipette (e.g. Matrix, cat. no. 8075+8076)
  96-well plate, flat-bottom (e.g. Nunc, 167008)
  Vitek2 system (Biomerieux) (only for comparative reasons)
  PC with the software Matlab® (version 7.5.0.342, The Mathworks, including the "Statistics" and "Image Processing" toolbox), ImageJ, the Matlab tool PHLIP[15], Auto PHLIP-ML v1.0.0[14] and IMARIS® x64 (version 5.7.2, Bitplane, not necessary for analysis), Microsoft Office Excel (or similar software)

Reagents Setup
Media
  LB medium is prepared by dissolving all components listed above (see REAGENTS) in 1 liter of distilled water and autoclaving. The medium is stable for ~3 months at room temperature (~22° C.).

Staining Solution
  BacLight stock solution must be prepared immediately before use. Both components of the LIVE/DEAD BacLight Bacterial Viability Kit (Syto9 and PI) are diluted in the ratio of 1:300 in sodium chloride solution containing 5% (vol/vol) DMSO.

Antibiotic Solutions
  Antibiotic stock solutions should be prepared less than 24 h before use. Antibiotics are dissolved in LB medium and filtered through a 0.22-μm sterilizing filter at the following concentrations: ciprofloxacin (CIP), 1.024 mg ml$^{-1}$; tobramycin (TM), 2.048 mg ml$^{-1}$; ceftazidime (CAZ), 2.048 mg ml$^{-1}$; and meropenem (MEM), 1.024 mg ml$^{-1}$. Serial dilutions of the stocks are prepared in LB medium immediately before use.

General Procedure for Biofilm Formation
I. Preparation of Pre-Cultures
The evening before the inoculation of the 96-well microtitre plates, inoculate bacteria from a single colony into 2 ml of LB medium in a tube and incubate the preculture in an orbital shaker (180 r.p.m.) at 37° C. overnight (~16 h). The next morning, prepare a subculture from the overnight culture by diluting it with fresh LB medium to an OD600 of 0.02. The total volume of the inoculated medium depends on the number of replicates and the number of antibiotics or antibiotic dilutions to be tested for this isolate.

II. Biofilm Growth
Take off the lid of the designated number of sterile half-area μClear microtitre plates and use 100 μl per well of the diluted overnight culture(s) (Step 2) to inoculate the wells (testing different antibiotics, antibiotic dilutions and a minimum of two replicates for each combination). Thereafter, seal the plate(s) with an air-permeable cover foil (no lid) and incubate for 24 h at 37° C. in an incubator with humid atmosphere.

III. Antibiotic-Treatment of the Biofilms
After 24 h of growth, the biofilms within the wells of the microtitre plate were exposed to antibiotics. Stock solutions of the chosen antibiotics in LB medium were prepared and two-fold serial dilutions in fresh LB-medium were performed. The following maximum concentrations are recommended: tobramycin 512 μg ml$^{-1}$, ciprofloxacin 256 μg ml$^{-1}$, ceftazidime 512 μg ml$^{-1}$ and meropenem 256 μg ml$^{-1}$. If the anti-biofilm activity of other antibiotics than those listed above should be tested, these should be tested at a maximum concentration of approximately 1,000× the minimal inhibitory concentration as determined in planktonic cultures. To add the antibiotic dilutions to the microtitre plates, the plates were taken out of the incubator into a safety cabinet. The cover foil was removed and 40 μl antibiotic solution to the appropriate well (different antibiotics/concentrations) were added except to the control well(s) where only LB is added.

IV. Staining of the Biofilms
Prepare staining solution as described above (see REAGENT SETUP). Add 20 μl of staining solution to each well directly after the addition of the antibiotic solution to achieve a final concentration of 1.4 μM of Syto9 and 8.3 μM of PI in the wells. Cover the microtitre plate with a fresh air-permeable foil and return the plate to the incubator. Continue incubation for 24 h at 37° C. before imaging. Immediately before microscopy (after ~48 h total incubation time), remove the microtitre plate with treated biofilms from the incubator.

V. Microscopy Automated Run or Manual Run

When using the automated confocal Opera system, two positions at the center of each well are chosen automatically to acquire z-stacks of the biofilms. The maximum height of the z-stacks, which has to be checked in advance for automated image acquisition, is adjusted at levels of the corresponding control sample (if multiple isolates are tested in one microtitre plate, acquisition settings can be defined in subsets). Focal planes are acquired starting from the bottom of the plate (position 0) with an interplane distance (z-step size) of 3 µm (using a 40×/0.85 numerical-aperture (NA) air objective). Syto9 is excited with a 488-nm laser and detected with a 540/75 nm band-pass emission filter, whereas PI is excited at 561 nm and detected with a 600/40 nm band-pass emission filter.

If a non-automated confocal microscope is used, choose adequate filter settings for Syto9 and PI. To enhance comparability, biofilm images should be recorded at the center of a well. In a manual process, due to time reasons image acquisition might be reduced to one stack per well if 2-3 replicates of the same sample are present within the plate.

VI. Data Analysis Computer Calculation

Save the image stacks as single .bmp image files (image files may require conversion, for example, with MATLAB software). Batch-process all images using a background subtraction tool (for example, the 'Subtract Background' command in ImageJ). Following background subtraction, use an Otsu-thresholding algorithm to obtain thresholded binary images (8-bit format). Reduce the appearance of planktonic bacteria and outlying pixels with a noise filter (such as the 'Remove Outliers' command in ImageJ). Steps 11-13 are exemplified in Supplementary FIG. 1. Reassemble the image stacks from the individual processed binary images for each position and channel with Auto PHLIP-ML software. Use the MATLAB-based tool PHLIP (without connected volume filtration) to calculate descriptive parameters of biofilms (including biovolume, substratum coverage, area-to-volume ratio, spatial spreading and 3D colocalization) from the integrated total of each individual slice of a thresholded z-stack. Calculate (with Microsoft Excel) the different proportions of green (live bacteria) as well as red and yellow/colocalized (dead bacteria) biovolumes from the analyzed stacks using the 'colocalization in 3D' value and the parameters 'red', 'green', and 'total biovolume' (in µm3) generated by the PHLIP software.

A biofilm is considered affected by an antibiotic within the given concentration range when there is a constant increase in the red+yellow (RY) biovolume fraction within the given antibiotic concentration range and this fraction is at least 80% of the total biovolume.

VII. Multi Species Biofilms

Sputum specimens obtained from two individual cystic fibrosis patients were obtained, resuspended in sodium-chloride solution (approx. 1:10) and incubated in LB medium for 24 hours before exposure to antibiotics (1 mg/ml). The following antibiotics were tested: ceftazidime, tobramycin and colistin. Image acquisition and data analysis were performed as described in steps V and VI.

Results

FIG. 1 shows the work-flow of the biofilm susceptibility test system as described herein.

To evaluate whether the optical analysis of biofilm bacteria grown in a 96-well plate could serve as a susceptibility testing method for biofilms of clinical *P. aeruginosa* isolates, we stained and monitored the proportion of live versus dead biofilm bacteria for PA14 and five clinical isolates under the addition of serially diluted antibiotics and compared these results with CFU counts. It is expected that if the biofilm is susceptible to the antibiotic being studied, the proportion of dead bacteria should increase with increasing antibiotic concentrations and the fraction of viable bacteria should decrease.

To show the reproducibility of the staining procedure, image acquisition and data analysis, we cultivated PA14 biofilms in a 96-well plate and compared the processed-image data of the fraction of red biovolume versus total biovolume (FIG. 2). We operated a 40×/0.85-numerical aperture air objective and obtained the physical biovolume parameters (in µm$^3$) from the individual thresholded image stacks of the Syto9 (green) and PI (red) dyes as well as the union of the virtually combined image stack of both dyes (green∪red) using PHLIP software. No major differences were observed in the relative fluorescent proportions (red/(green∪red)) of the stained bacteria among the biofilms of individual wells, indicating the robustness of the procedure. Thus, the method and system according to the present invention allows to establish reproducibly multiple equivalent biofilms, thus, providing a robust anti-microbial susceptibility assay.

To further validate the accuracy of the staining procedure under the selected experimental conditions, we treated biofilms of three clinical isolates with isopropanol, stained the isolates with Syto9 and PI, acquired image stacks, rebuilt the 3D image structure and performed data analysis on the basis of thresholded image stacks. Although all bacteria were efficiently killed by the addition of isopropanol, as verified by CFU counts (data not shown), we detected not only red fluorescence but also a large fraction of yellow (overlapping red and green signals) fluorescence and a minor fraction of green fluorescence (10-20%) (FIG. 3).

The green DNA-intercalating dye (Syto9) is membrane permeant and thus stains all bacteria, whereas the red dye (PI) stains only the DNA of dead bacteria. In dead cells, PI displaces Syto9 because of a stronger affinity to DNA and thus quenches the Syto9 emission. Staining is strongly dependent on the relative concentrations of the two dyes; visualization of stained bacteria is influenced by the microscope's exposure and detector settings. The visualization of a constant fraction of green bacteria in a killed biofilm population is most likely due to an insufficient decomposition of red and green fluorescence and can be improved by acquiring the images at a higher magnification (data not shown). Furthermore, within the fraction of dead bacteria, an incomplete displacement of Syto9 by PI leads to a combined red and green fluorescent signal, producing a yellow fluorescence overlap. Accordingly, red and green colocalization is particularly observable when staining extracellular DNA. As it is well documented that biofilm bacteria express increased antibiotic resistance, we tested the following antibiotic concentration ranges: 2-512 µg ml$^{-1}$ of TM, 0.5-256 µg ml$^{-1}$ of MEM, 2-512 µg ml$^{-1}$ of CAZ and 0.5-256 µg ml$^{-1}$ of CIP. Conventional Clinical and Laboratory Standards Institute (CLSI; formerly National Committee for Clinical Laboratory Standards) break points for MIC determinations consider only parenteral amounts and do not take into account these high antimicrobial concentrations. However, inhaled administration of antibiotics (such as TM)

assures high concentrations in the CF lung, thus improving the therapeutic ratio over that of parenterally administered antibiotics.

In FIG. 4, the fractions of red, green and yellow/colocalized biovolumes calculated from the thresholded image stacks (Syto9 and PI stacks) are shown. Note that the physical biovolume parameters are mean values calculated from the integrated total of each individual slice of a thresholded z-stack. The CFU determinations of PA14 and five clinical strains under the addition of various concentrations of TM are also depicted in FIG. 4. Because the separation of planktonic and biofilm bacteria was not possible for all tested isolates, CFU determinations were performed using the whole content of the well including both planktonic and biofilm bacteria.

The addition of TM showed a clear effect on the PA14 wild type and the clinical isolates 5497 and 5520. The fraction of the RY biovolume constantly increased with increasing antibiotic concentrations and reached ~80% of the total biovolume (comparable with isopropanol treatment), whereas the CFU counts in these three strains decreased to ≤$10^5$ cells per ml. The steep decline in CFU counts as opposed to the more gradual increase in the fraction of dead cells can be explained by the fact that, whereas CFU counts reflect viability within the whole biofilm-containing well (including planktonic cells, which are efficiently killed even by low antibiotic concentrations, the calculations of biovolume proportions explicitly exclude signals from planktonic bacteria.

The PA14 control already showed a very high proportion of dead cells (FIG. 4), although no antibiotics were added and the CFU counts indicated an untreated control level. This fraction of dead cells decreased when effective antibiotics were added at low concentrations. This seemingly contradictory finding is especially apparent in strains that produce high-biomass biofilms, and it might be explained by a weak or insufficient staining with Syto9. It does not seem to be to the result of an induction of biofilm formation by the aminoglycoside, as we did not observe an increase in biofilm biomass (data not shown).

In contrast to the three responsive strains (PA14, 5497 and 5520), we observed a constant fraction of RY biovolume that remained below 80% in the other three strains (5522, 5524 and 5529). CFUs showed a minor decrease at low antibiotic concentrations; however, this was most probably due to the killing of planktonic bacteria surrounding the biofilm. In strain 5529, the fraction of the RY biovolume reached nearly 80% of the total biovolume only at very high concentrations (512 µg ml$^{-1}$), which might indicate a responsiveness of this strain to these very high antibiotic concentrations.

The distribution of the biovolume proportions and CFU counts for MEM, CAZ and CIP is depicted in FIGS. 5, 6 and 7.

In contrast to the results obtained with TM, all strains showed resistance to MEM under biofilm growth conditions. We did not observe an increase in the fraction of the RY biovolume within the given MEM concentration range, and in no strain did the RY fraction reach 80% of the total biovolume. Furthermore, with the exception of strain 5529 at very high MEM concentrations (128 µg ml$^{-1}$), we did not observe a reduction in CFU counts (to ~$10^6$ cells per ml) FIG. 5).

Similarly, CAZ did not prove to be a very efficient antibiofilm antibiotic in the clinical strains tested. An increase in the fraction of RY biovolume was observed only in strain 5497. In this case, the RY biovolume reached almost 80% of the total biovolume and was correlated with a decrease in CFU count to $10^6$ cells per ml. In almost all other strains, we observed neither an increase in the fraction of the RY biovolume nor a decreased CFU count within the CAZ concentration range of 0.5-512 µg ml$^{-1}$ (FIG. 6). An exception was PA14, which showed a decrease in CFU count to $10^6$ cells per ml without correlated imaging data. The reason for this is not known, and it may have been the result of incorrect CFU determinations, as the total biomass did not significantly decrease after antibiotic treatment (data not shown). Ciprofloxacin killed the biofilm bacteria more efficiently. With the exception of the two clinical strains 5522 and 5524, we observed a strong increase in the fraction of RY biovolumes in all strains (FIG. 7); the RY fraction in these strains reached nearly 80% of the total biovolume. These increases were also associated with steep decreases in CFU counts. We conclude that our optical system is capable of determining the effectiveness of a given antibiotic concentration range against P. aeruginosa biofilms. An overall constant increase in the fraction of dead bacteria reaching ~80% (of total biovolume) corresponded well to biofilm responsiveness at a given concentration range (as corroborated by CFU counts). Most remarkably, the effectiveness of an antibiotic against biofilm-grown bacteria could not be predicted from MIC profiles, as we observed marked differences in the responsiveness of the biofilms of the various clinical strains, even if they showed the same MIC values when grown under planktonic conditions (Table 1).

We further clarified whether this approach can also be used for susceptibility testing of mixed bacterial communities. We diluted sputum specimens taken from two individuals with CF and incubated them in LB medium for 24 h before exposure to antibiotics (1 mg ml$^{-1}$). As depicted in FIG. 8, the structure and profile of the two samples significantly differed: whereas one sample was responsive to colistin, the other was not.

Our experiments suggest that this method is a rapid and robust microtitre plate-based model for the formation of P. aeruginosa biofilms and that it can be used to identify antimicrobial resistance under biofilm growth conditions. In addition, this method can serve to identify the capability of various P. aeruginosa strains and mutants to form biofilms or to test the impact of novel antimicrobial compounds on bacterial biofilms even multi-species communities.

This experimental setting represents a rapid and robust 96 well-microtitre based model for the formation of P. aeruginosa biofilms and can not only be used to identify antimicrobial resistance under biofilm growth conditions but may furthermore serve as an fast and easy assay to test the capability of various P. aeruginosa strains and mutants to form biofilms.

To demonstrate the usefulness of the method and system for structural discrimination according to the present invention, the capability of PA14 intents to form biofilms were tested. In contrast to the example described above, image stacks of the biofilms were acquired after 72 h instead of 48 h. Moreover, a 20×/0.4 NA air objective was used, increasing the area of interest to improve statistical significance on the cost of resolution. Furthermore, data analysis is dependent on all PHLIP-derived values to allow more efficient discrimination of biofilm phenotypes.

Biofilm Growth Assays.

To assess the capability of the transposon mutants of the Harvard PA14 library to produce biofilms, 5 ml samples of a thawed mutant stock were transferred into 150 ml Luria-Bertani (LB) broth within a 96-well plate. The preculture plate was covered with an air-permeable BREATHseal cover foil (Greiner Bio-One) and incubated at 37° C. on a shaking unit. After 4 h, 5 ml of the precultures of each well/mutant were transferred to 100 ml LB medium within a sterile half-area 96-well µClear microplate (Greiner Bio-One). The plates were sealed with a new air-permeable cover foil and placed in an incubator with a humid atmosphere. The image-based screen was carried out after 70 h of incubation. The incubation was paused after 24 h in order to stain the bacteria with the LIVE/DEAD BacLight Bacterial Viability kit (Molecular Probes/Invitrogen). A 50 ml volume of diluted staining solution was added to each well, resulting in a final concentration of 1.4 mM Syto9 and 8.3 mM propidium iodide (PI). In each plate, internal controls, representing the PA14 wild-type, and reduced and enhanced biofilm producers, were added (the last control was only included in roughly half of the plates). The PA14 NR pqsA transposon mutant served as a control for poor biofilm formation, whereas an flgF mutant derived from the PA14 wild-type served as the control for enhanced biofilm formation.

Automated Confocal Microscopy.

The image-based screen was carried out using the Opera system (Perkin-Elmer—Cellular Technologies), a fully automated confocal microscope suited for the analysis of samples grown in microtitre plates. This system allowed automatic selection of the experimental parameters for image acquisition, which could be applied over the entire screen in order to minimize plate-to-plate variability.

Two positions in each well were chosen to acquire z-stacks of the biofilms. Since the biofilms were grown on a polystyrene foil, which may sag slightly in the centre between the edge fixing points, the z-stacks were positioned in the centre of each well. A total biofilm height of 30 mm was imaged at 11 focal planes starting from the bottom of the plate (position 0), with an inter-plane distance (z-step size) of 3 mm, using a 20×/0.4 NA air objective. Syto9 was excited with a 488 nm laser and detected with a 540/75 nm bandpass (BP) emission filter, whereas PI was excited at 561 nm and detected with a 600/40 nm BP emission filter. Moreover, we selected a dual consecutive exposure mode to prevent optical cross-talk.

Data Analysis.

Image stacks obtained by fluorescence microscopy were converted to single '.bmp' files with the software Matlab (version 7.5.0.342, The Mathworks) and further processed to obtain thresholded binary images using the Otsu thresholding algorithm. Afterwards, stacks for each position and dye were reassembled with the software Auto PHLIP-ML (v1.0.0)[14], now containing thresholded binary images instead of raw images. Analysis of the different stacks was performed with the Matlab-implemented tool PHLIP[15], producing the following descriptive parameters for the physical properties of the biofilms: biovolume, substratum coverage, area-to-volume ratio, spatial spreading (horizontal, vertical and total), mean thickness and roughness. For the eight parameters extracted from both the Syto9 and the PI image stack, a mean value of the two stack positions was calculated for each mutant. These multidimensional data were visualized within a 2D projection with a dimensionality reduction method based on singular value decomposition. The dataset was furthermore the basis to distinguish the different biofilm phenotypes of the mutants and to categorize them into wild-type-like (normal biofilm), poor (reduced biofilm) and thick (enhanced biofilm) biofilm producer via cluster analysis (k-means clustering) performed with the software Rapidminer [version 4.3]. Although the use of a 20×/0.4 NA air objective does not allow the discrimination of live and dead bacteria at the single-cell level, we monitored both red and green fluorescence, because some biofilms exhibited very characteristic staining patterns, thus facilitating the differentiation of biofilm production in the various mutants. 3D visualization of the biofilm was realized with the software IMARIS ×64 (version 5.7.2, Bitplane).

Global Screen to Identify Genetic Determinants of Biofilms.

That is, the aim of this study was to identify P. aeruginosa PA14 mutants exhibiting an altered biofilm phenotype on a global scale. While multiple genetic screens for modified biofilm formation have been performed in a broad range of bacterial pathogens, including P. aeruginosa, this is the first example of a screen for mutants forming altered 3 day old biofilms.

5832 mutants of the PA14 transposon insertion library[13] were grown in 96-well microtitre plates for 72 hours in rich medium. An example of the normal biofilm phenotype represented by the PA14 wild-type in comparison to a poor biofilm producer (the pqsA mutant) and a mutant that produced thick biofilms (the flgF mutant) is depicted in FIG. 9. A hierarchical cluster tree demonstrates the successful discrimination of replicates of four different mutants, which is based on the PHLIP-calculated physical parameters of the biofilms.

In order to ascertain the sensitivity and specificity of the screening method the wild-type and the poor biofilm control were included in each 96-well screening plate, whereas the enhanced biofilm control was added into roughly half of the microtitre plates.

A 2D-projection based on singular value decomposition of the 16 discriminative parameters of all 5832 mutants in addition to 536 internal controls is shown in FIG. 10. The boundaries of the three groups including mutants with reduced, normal and enhanced biofilms were defined following k-means clustering and optimized by the minimization of false-positive and false-negative controls in the respective clusters. The internal controls are highlighted to visualize the distribution into the three clusters.

In Table 2 the PA 14 mutant subgroup exhibiting poor biofilms as compared to the wild-type is listed. This subgroup comprised 7% of all tested mutants, 81.7% of all poor biofilm controls, only 11.6% of the PA14 wild-type and none of the PA14 enhanced biofilm controls. Vice versa Table 3 lists the PA14 mutant subgroup which comprises roughly 5% of all mutants exhibiting an enhanced biofilm phenotype. This mutant subgroup included 50% of all enhanced biofilm controls, only 8.9% of the PA14 wild-type and none of the PA14 poor biofilm control. Interestingly, among the mutants with defective biofilm formation 68.3% of the affected genes were encoding for hypothetical proteins, whereas 71.2% of the enhanced biofilm forming mutants were encoding for hypothetical proteins. These data indicate that there seem to be many yet to be discovered regulatory cascades required for biofilm development.

Rare Detection of Previously Identified Genetic Determinants of Biofilm Formation.

Our approach uncovered 394 (Table 2) and 285 (Table 3) genetic determinants that contribute to the biofilm phenotype of P. aeruginosa PA14. Only very few of these genes have previously been detected in global screens for factors participating in biofilm formation in P. aeruginosa or various other bacterial pathogens. The main reason for this discrepancy seems to be that, whereas previous screens focussed on the identification of genes involved in the initial steps of adhesion, we analysed biofilms.

The first global genetic screen for mutants that form altered biofilms in P. aeruginosa has been performed by O'Toole & Kolter in (1998)[15], which uncovered 15 surface attachment deficient (sad) mutants. None of these mutants was detected within our screen. Instead, we observed that sad mutants with defects in swimming motility produced thicker biofilms than the wild-type. This apparent inconsistency strongly supports the previous finding that the requirement for flagella-driven motility for the establishment of biofilms can vary depending on environmental conditions. Whereas O'Toole & Kolter used minimal medium to cultivate the Pseudomonads in microtitre plates at the air-liquid interface, a rich medium (LB broth) was used herein to promote biofilm formation at the bottom of the microtitre plate under low oxygen conditions.

Genetic Determinants Promoting Survival Under Microaerophilic Conditions are Essential for Efficient *P. aeruginosa* Biofilm Formation.

Among the 394 biofilm-deficient mutants, the two main components of the rhl quorum sensing system, rhlR and rhlI were identified. The rhl system is known to be highly expressed under biofilm and microaerophilic conditions and *P. aeruginosa* has been shown to form robust anaerobic biofilms, the viability of which requires the rhl quorum sensing system. Rhl mutants exhibited high levels of toxic NO, which seems to account for a premature cell death. Further, an oprF mutant to form poor biofilms was identified using the screening assay according to the present invention. OprF has been shown to be highly expressed in clinical cystic fibrosis *P. aeruginosa* isolates. A proteomic analysis revealed a markedly up-regulation of OprF under anaerobic conditions and OprF has been suggested be important for NO detoxification and thus for the establishment of biofilms.

Two poor biofilm mutants affected in genes with predicted terminal oxidases activity were identified. One of them has been described to be preferentially expressed in stationary phase of growth (CoxA) and the other, a cyanide insensitive bd-type oxidase (cio), was predicted to have a high affinity for oxygen and was shown to contribute together with the $cbb_3$-1 and $cbb_3$-2 oxidases to sustain respiration when oxygen levels are low[15]. No mutants of the $cbb_3$ oxidases to exhibit a reduced biofilm phenotype were identified. However, a clear defective biofilm formation in the cioB mutant was observed, although a cioA mutant was described to exhibit similar biofilm formation capabilities as the wild-type when grown in a flow chamber[15]. Interestingly, the work from the Harwood group[15] showed that expression of the hydrogen cyanide synthase genes was activated about fivefold in a transcriptome analysis under microaerophilic conditions and suggested that the cyanide insensitive oxidase might exert the additional role of protecting the cells from hydrogen cyanide toxicity during microaerophilic growth. This scenario might be of major importance under the experimental conditions according to the present invention and might also explain why cultivation of a cioA mutant within the flow chamber does not show a biofilm defective phenotype because HCN is more efficiently eliminated.

Furthermore, it is interesting to note, that with the method according to the present invention, additional poor biofilm mutants that were affected in genes described to be pronouncedly up-regulated under microaerophilic/anaerobic growth conditions, including hutU encoding an urocanase[16], PA4142, a conserved hypothetical gene within the operon encoding a predicted 4Fe-4S ferredoxin transmembrane protein and a homologue of the catalytic subunit of cbb3 oxidase (CcoN), PA5481, azu, nirE, nirJ, nosL and ptxR.

Arginine Metabolism is Essential for *P. aeruginosa* Biofilms.

When oxygen availability becomes limited a central metabolic process to generate ATP in *P. aeruginosa* is arginine fermentation via the arginine deaminase pathway (ADI). Although no mutants affected in the ADI pathway were found to exhibit a reduced biofilm formation phenotype, it is interesting to note, that several mutants with insertions within genes involved in the pyrimidine nucleotide biosynthetic pathway (pyrBC, carAB) were identified. The first step in this pathway is the formation of carbomyl-phosphate by the carbomyl-phosphate synthase, which is encoded by the carAB genes. Carbomyl-phosphate is also required for the biosynthesis of arginine from ornithine via the arginine metabolic pathway involving argFGH. Not only mutants affected in the pyrimidine nucleotide biosynthetic pathway were identified but also an argG and argH mutant involved in the formation of arginine from carbomyl-phosphate and ornithine, and two mutants (gabT and aruG) involved in arginine and ornithine degradation, respectively. It therefore seems that *P. aeruginosa* PA14 requires a functional arginine metabolism in order to establish robust biofilms, thereby arginine probably serves as a source of carbon, energy and nitrogen.

Furthermore, a mutant with an insertion within the cbrA gene which exhibited a reduced biofilm phenotype was identified. It has previously been shown that CbrAB is a two-component system essential for the expression of ArgR-dependent pathways. Since ArgR is the major regulator of arginine and glutamine metabolism this finding underscores the importance of arginine metabolism for the establishment of *P. aeruginosa* biofilms.

Most interestingly, in *Vibrio parahaemolyticus* a carA transposon mutant has been shown to form only thin pellicles at the air-medium interface, and a comparison of the previously published transcriptome profiles of *S. aureus*, *Legionella pneumophila* and *E. coli* revealed a common set of highly expressed genes under biofilm conditions that are involved in the pyrimidine nucleotide biosynthetic pathway as well as arginine metabolism. PyrRPBC, carAB, pyrFE, argDABC and argGH were highly expressed in *S. aureus* biofilms pyrGH, carA and argD in *L. pneumophila* biofilms and artJ, pyrB, pyrI gltB, glnA, gltD, argC and argF in *E. coli* biofilms, indicating that a functional arginine metabolism is essential for biofilm formation in various bacterial species.

The pH Homeostasis is Essential for *P. aeruginosa* Biofilms.

One of the most extensively differentially regulated genes, which was identified in the first screen for the global *P. aeruginosa* gene expression profile under biofilm growth conditions was ureB encoding for an urease[17]. This enzyme was described to be markedly up-regulated in *Streptococcus salivarius* and *S. aureus* biofilms and its involvement in the maintenance of pH homeostasis of biofilm cultures has been speculated. Ureases hydrolyse urea to two molecules of ammonia and one of carbon dioxide, which results in efficient alkalinization of the environment as an alternative to generate ammonia from the arginine deaminase pathway. The findings described herein indicate that pH homeostasis is crucial to PA14 biofilm formation in our experimental setting. Not only various mutants affected in the arginine metabolism (see above) to exhibit poor biofilms but also an ureB mutant, which produced low levels of biofilms were found. Furthermore a kdpD mutant to develop poor biofilms was identified. In addition to the production of ammonia, cation transport ATPases, such as the high affinity $K^+$-specific transport system encoded by the kdp operon, can also contribute to pH homeostasis through the exchange of $K^+$ for $H^+$. In *E. coli*, KdpD and KdpE, proteins that control expression of the kdpFABC operon, are members of the class of sensor kinase/response regulator proteins.

Genes Essential for the Repair and Maintenance of DNA are Required for Efficient Biofilm Formation.

The screen for biofilm deficient mutants uncovered the importance of 6 genes involved in DNA repair mechanisms (recA, recB, recG, recJ, recN, and uvrD). RecA has very recently been described to affect biofilm development in Streptococcus mutants. Most interestingly, in P. aeruginosa it was demonstrated that double-strand DNA break repair is required for biofilm-mediated diversity and that an endogenous oxidative stress triggers a DNA repair mechanism that in turn generates genetic variants with a wide range of fitness characteristics[18]. It therefore seems that mutants with defects in the generation of a self-induced diversity do not withstand the intrinsic and extrinsic stresses that act upon the biofilm bacteria in our 96-well format system.

Interbacterial Signalling Contributes to Biofilm Formation.

In addition to the mutants within the rhl quorum sensing system a mexH and mexI mutant to form deficient biofilms were identified. The MexH protein was recently described to be up-regulated at the protein level during biofilm development and to play a critical role in biofilm maturation. This might be due to the influence of the MexGHI-OpmD pump on interbacterial communication, since a recent report showed that mutation of genes encoding the pump resulted in the inability to produce N-(3-oxododecanoyl)-L-homoserine lactone (3-oxo-c12-hsl) and 4-quinolones. The screen as described herein identified pqsA and pqsC mutants as poor biofilm producers, which is in agreement with the finding showing that a diminished 4-quinolone production resulted in low biofilm production. Interestingly, mutations within the pyrimidine pathway (carB, pyrB and pyrD) have previously been described to exhibit a reduced production of the 4-quinolones, which could be complemented in both, growth and 4-quinolone production, by the exogenous addition of UMP. Although the low 4-quinolone production may contribute to the low biofilm production of the pyrimidine mutants, the finding that enzymes of the pyrimidine biosynthetic pathway are up-regulated under biofilm growth conditions in various bacterial pathogens (see above) suggests that other mechanisms such as the requirement for arginine might also contribute to the poor biofilm formation.

REFERENCE LIST

1. Costerton, J. W., et al., *Science* 284, 1318-1322 (1999).
2. Parsek, M. R. & Singh, P. K., *Annu. Rev. Microbiol.* 57, 677-701 (2003).
3. Hoyle, B. D. & Costerton, J. W., *Prog. Drug Res.* 37, 91-105 (1991).
4. Gilbert, P., et al., *Adv. Microb. Physiol* 46, 202-256 (2002).
5. Smith, A. L., et. al., *Chest* 123, 1495-1502 (2003).
6. Keays, T. et al., *J. Cyst. Fibros.* 8, 122-127 (2009).
7. Ceri, H. et al., *J. Clin. Microbiol.* 37, 1771-1776 (1999).
8. Pierce, C. G. et al., *Nat. Protoc.* 3, 1494-1500 (2008).
9. Falcioni, T., Papa, S. & Gasol, J. M., *Appl. Environ. Microbiol.* 74, 1767-1779 (2008).
10. Boulos, L., et al., *J. Microbiol. Methods* 37, 77-86 (1999).
11. Peeters, E., Nelis, H. J. & Coenye, T., *J. Microbiol. Methods* 72, 157-165 (2008).
12. Harrison, J. J. et al., *Biol. Proced. Online.* 8, 194-215 (2006).
13. Liberati, N. T. et al., *Proc. Natl. Acad. Sci. USA* 103, 2833-2838 (2006).
14. Jacobs, M. A., et al., (2003), *Proc Natl Acad Sci USA* 100, 14339-14344.
15. Alvarez-Ortega, C. & Harwood, C. S. (2007), *Mol Microbiol* 65, 153-165.
16. O'Toole, G. A. & Kolter, R. (1998), *Mol Microbiol* 30, 295-304.
17. Whiteley, M., et al., (2001), *Nature* 413, 860-864.
18. Boles, B. R. & Singh, P. K. (2008), *Proc Natl Acad Sci USA* 105, 12503-12508.
14. Merod, R. T., et al., (2007). *Appl Environ Microbiol* 73, 4922-4930.
15. Mueller, L. N., et al., (2006), BMC Ecol 6, 1.

TABLE 1

Results of the planktonic and biofilm susceptibility tests.

| | ceftazidime | | ciprofloxacin | | meropenem | | tobramycin | |
| --- | --- | --- | --- | --- | --- | --- | --- | --- |
| isolate | MIC[1] | biofilm response[2] | MIC[1] | biofilm response[2] | MIC[1] | biofilm response[2] | MIC[1] | biofilm response[2] |
| PA14 | <=1.0 (S) | — | <=0.25 (S) | ✓ | <=0.25 (S) | — | 1.0 (S) | ✓ |
| 5497 | 1.0 (S) | ✓ | 0.5 (S) | ✓ | <=0.25 (S) | — | <=0.25 (S) | ✓ |
| 5520 | 4.0 (S) | — | 2.0 (I) | ✓ | 0.5 (S) | — | 1.0 (S) | ✓ |
| 5522 | 4.0 (S) | — | 2.0 (I) | — | 2.0 (S) | — | >32.0 (R) | — |
| 5524 | 2.0 (S) | — | 1.0 (S) | — | <=0.25 (S) | — | 1.0 (S) | — |
| 5529 | <=1.0 (S) | — | 1.0 (S) | ✓ | 1.0 (S) | — | >32.0 (R) | — |

[1]Minimal inhibitory concentrations (μg ml$^{-1}$) and interpretation category results (S: sensitive, I: Intermediate and R: resistant) were obtained using the Vitek2 system
[2]Biofilms were categorized as responsive (✓) if a consistent increase in the fraction of red and yellow (colocalized) fluorescenct biovolume (reaching ~ 80% of the total biovolume) within a given antibiotic concentration range was detected.

TABLE 2

List of PA14 mutants exhibiting reduced biofilm formation as compared to the wild-type, determined by microscopic analysis.

| PAO1 ortholog | PA14 gene locus | Mutant-ID | Gene name |
| --- | --- | --- | --- |
| | | 29412 | |
| | | 29626 | |
| | | 29956 | |
| | | 30257 | |
| | | 31629 | |
| | | 31910 | |
| | | 33277 | |
| | | 33357 | |
| | | 33798 | |
| | | 34236 | |
| | | 37777 | |
| | | 38019 | |
| | | 41463 | |
| | | 41493 | |
| | | 41885 | |
| | | 42394 | |
| | | 54696 | |

TABLE 2-continued

List of PA14 mutants exhibiting reduced biofilm formation as compared to the wild-type, determined by microscopic analysis.

| PAO1 ortholog | PA14 gene locus | Mutant-ID | Gene name |
|---|---|---|---|
| | | 56291 | |
| | PA14_00980 | 31866§ | |
| | PA14_10960 | 30692 | |
| | PA14_15380 | 52851 | |
| | PA14_15460 | 38000 | merA |
| | PA14_15580 | 6305‡ | |
| | PA14_20600 | 33533 | |
| | PA14_23420 | 39858 | ORF_10 |
| | PA14_28850 | 52683 | |
| | PA14_30970 | 42107‡ | |
| | PA14_31090 | 231 | |
| | PA14_33320 | 23117 | |
| | PA14_33340 | 30482‡ | |
| | PA14_49720 | 32032 | |
| | PA14_51640 | 36907 | |
| | PA14_51840 | 34822‡ | |
| | PA14_56970 | 24356 | |
| | PA14_59410 | 31895‡ | |
| | PA14_59780 | 32292‡ | rcsC |
| | PA14_59970 | 41972 | |
| PA0020 | PA14_00210 | 42877 | |
| PA0054 | PA14_00660 | 28905 | |
| PA0075 | PA14_00890 | 31907 | |
| PA0090 | PA14_01100 | 56461‡ | |
| PA0106 | PA14_01300 | 31674‡ | coxA |
| PA0107 | PA14_01310 | 27137 | |
| PA0117 | PA14_01430 | 30201 | |
| PA0124 | PA14_01510 | 29203 | |
| PA0126 | PA14_01540 | 31932 | |
| PA0133 | PA14_01640 | 23101 | |
| PA0150 | PA14_01860 | 41199 | |
| PA0159 | PA14_01980 | 39380 | |
| PA0165 | PA14_02060 | 27092‡ | |
| PA0179 | PA14_02260 | 28135 | |
| PA0189 | PA14_02370 | 31768 | |
| PA0190 | PA14_02380 | 42044 | |
| PA0208 | PA14_02550 | 29044§ | mdcA |
| PA0224 | PA14_02740 | 24637‡ | |
| PA0228 | PA14_02790 | 31822 | pcaF |
| PA0252 | PA14_03110 | 39716 | |
| PA0266 | PA14_03450 | 27864‡ | gabT |
| PA0290 | PA14_03790 | 41840 | |
| PA0309 | PA14_04040 | 25951 | |
| PA0340 | PA14_04440 | 45778‡,§ | |
| PA0370 | PA14_04860 | 41284 | |
| PA0401 | PA14_05250 | 38595‡ | |
| PA0402 | PA14_05260 | 52690† | pyrB |
| PA0413 | PA14_05390 | 35863 | chpA |
| PA0438 | PA14_05700 | 38090‡ | codB |
| PA0439 | PA14_05740 | 31070‡ | |
| PA0441 | PA14_05770 | 28218 | dhT |
| PA0491 | PA14_06400 | 41935‡ | |
| PA0496 | PA14_06480 | 30310‡ | |
| PA0510 | PA14_06660 | 29167 | nirE |
| PA0511 | PA14_06670 | 24114 | nirJ |
| PA0537 | PA14_06990 | 31133 | |
| PA0543 | PA14_07050 | 32832 | |
| PA0554 | PA14_07210 | 31761‡ | |
| PA0579 | PA14_07560 | 55455 | rpsU |
| PA0593 | PA14_07740 | 40435‡ | pdxA |
| PA0597 | PA14_07790 | 31210 | |
| PA0604 | PA14_07870 | 24388‡ | |
| PA0613 | PA14_07980 | 33288 | |
| PA0617 | PA14_08020 | 40962 | |
| PA0635 | PA14_08230 | 40570 | |
| PA0650 | PA14_08350 | 39937 | trpD |
| PA0660 | PA14_08460 | 37535 | |
| PA0708 | PA14_55150 | 41818 | |
| PA0723 | PA14_48940 | 25468 | coaB |
| PA0732 | PA14_54810 | 32764‡ | |
| PA0788 | PA14_54080 | 33775 | |
| PA0792 | PA14_54000 | 30372‡ | prpD |
| PA0826 | PA14_53620 | 23095 | |
| PA0828 | PA14_53550 | 39658 | |
| PA0854 | PA14_53220 | 41127‡ | fumC2 |
| PA0870 | PA14_53010 | 37388 | phhC |
| PA0897 | PA14_52690 | 24118 | aruG |
| PA0913 | PA14_52460 | 40905‡ | mgtE |
| PA0950 | PA14_51980 | 32890‡ | |
| PA0962 | PA14_51830 | 32034 | |
| PA0976 | PA14_51670 | 31914 | |
| PA0996 | PA14_51430 | 23621 | pqsA |
| PA0998 | PA14_51410 | 32423 | pqsC |
| PA1018 | PA14_51160 | 24077 | |
| PA1025 | PA14_51070 | 35365 | |
| PA1032 | PA14_50980 | 6114‡ | |
| PA1039 | PA14_50900 | 30978 | |
| PA1044 | PA14_50850 | 31842 | |
| PA1046 | PA14_50830 | 29696‡ | |
| PA1058 | PA14_50690 | 41941 | |
| PA1085 | PA14_50380 | 48300‡,§ | flgJ |
| PA1124 | PA14_49840 | 31934‡ | dgt |
| PA1126 | PA14_49810 | 39750 | |
| PA1144 | PA14_49610 | 35284‡ | |
| PA1167 | PA14_49320 | 30058 | |
| PA1195 | PA14_48840 | 57056 | |
| PA1214 | PA14_48610 | 31864 | |
| PA1226 | PA14_48420 | 40024 | |
| PA1229 | PA14_48390 | 31852‡ | |
| PA1231 | PA14_48350 | 33322 | |
| PA1232 | PA14_48340 | 40142 | |
| PA1237 | PA14_48280 | 28159‡ | |
| PA1242 | PA14_48170 | 29944 | |
| PA1243 | PA14_48160 | 40171 | |
| PA1259 | PA14_47930 | 6310‡ | |
| PA1262 | PA14_47900 | 32651 | |
| PA1263 | PA14_47890 | 25415 | |
| PA1275 | PA14_47730 | 34720‡ | cobD |
| PA1316 | PA14_47230 | 23390§ | |
| PA1326 | PA14_47100 | 31946‡ | ilvA2 |
| PA1356 | PA14_46750 | 40462 | |
| PA1429 | PA14_45970 | 25088 | |
| PA1458 | PA14_45590 | 5697*,‡ | |
| PA1467 | PA14_45460 | 33287 | |
| PA1486 | PA14_45210 | 28968 | |
| PA1507 | PA14_44950 | 29504‡ | |
| PA1522 | PA14_44760 | 40117 | |
| PA1533 | PA14_44620 | 27621 | |
| PA1555 | PA14_44360 | 40719‡ | |
| PA1588 | PA14_43950 | 46221‡ | sucC |
| PA1589 | PA14_43940 | 46283 | sucD |
| PA1592 | PA14_43900 | 6472 | |
| PA1636 | PA14_43350 | 31640‡ | kdpD |
| PA1643 | PA14_43270 | 30059‡ | |
| PA1662 | PA14_42980 | 35888 | |
| PA1668 | PA14_42910 | 31101 | |
| PA1677 | PA14_42820 | 41922‡ | |
| PA1681 | PA14_42760 | 35876‡ | aroC |
| PA1714 | PA14_42380 | 54358‡ | |
| PA1746 | PA14_41970 | 30103 | |
| PA1775 | PA14_41590 | 23226‡ | |
| PA1777 | PA14_41570 | 23102* | oprF |
| PA1797 | PA14_41280 | 29357 | |
| PA1812 | PA14_41090 | 29217‡ | mltD |
| PA1878 | PA14_40220 | 23537 | |
| PA1889 | PA14_40080 | 31798‡ | |
| PA1891 | PA14_40060 | 28321 | |
| PA1944 | PA14_39390 | 40566‡ | |
| PA1990 | PA14_38770 | 33304* | |
| PA2007 | PA14_38550 | 6180 | maiA |
| PA2040 | PA14_38140 | 28350‡ | |
| PA2079 | PA14_37630 | 31937‡ | |
| PA2121 | PA14_37140 | 35425 | |
| PA2125 | PA14_37090 | 25885 | |
| PA2127 | PA14_37070 | 27747‡ | |
| PA2130 | PA14_37030 | 30364‡ | cupA3 |
| PA2172 | PA14_36500 | 30530‡ | |
| PA2211 | PA14_36110 | 29219 | |

TABLE 2-continued

List of PA14 mutants exhibiting reduced biofilm formation as compared to the wild-type, determined by microscopic analysis.

| PAO1 ortholog | PA14 gene locus | Mutant-ID | Gene name |
|---|---|---|---|
| PA2212 | PA14_36100 | 24548 | pdxA |
| PA2258 | PA14_35380 | 31947 | ptxR |
| PA2301 | PA14_34850 | 33382 | |
| PA2379 | PA14_33890 | 27892 | |
| PA2423 | PA14_33290 | 25793 | |
| PA2469 | PA14_32700 | 31959 | |
| PA2484 | PA14_32500 | 24586‡ | |
| PA2518 | PA14_32080 | 26718§ | xylX |
| PA2561 | PA14_31400 | 45835 | |
| PA2580 | PA14_30740 | 32049 | |
| PA2593 | PA14_30560 | 25773§ | |
| PA2620 | PA14_30230 | 39351‡ | clpA |
| PA2623 | PA14_30190 | 24545‡ | icd |
| PA2642 | PA14_29940 | 39559‡ | nuoG |
| PA2643 | PA14_29930 | 34596 | nuoH |
| PA2649 | PA14_29850 | 24344‡ | nuoN |
| PA2673 | PA14_29530 | 41700 | |
| PA2684 | PA14_29400 | 41007 | |
| PA2692 | PA14_29300 | 29679 | |
| PA2759 | PA14_28410 | 23041 | |
| PA2779 | PA14_28140 | 39365 | |
| PA2780 | PA14_28130 | 23942‡ | |
| PA2791 | PA14_28020 | 40883 | |
| PA2794 | PA14_27990 | 25090‡ | |
| PA2828 | PA14_27500 | 33272‡ | |
| PA2839 | PA14_27390 | 37258 | |
| PA2884 | PA14_26770 | 38431 | |
| PA2901 | PA14_26550 | 31667‡ | |
| PA2931 | PA14_26140 | 28224 | |
| PA2954 | PA14_25830 | 22339 | |
| PA2956 | PA14_25810 | 24515 | |
| PA2958 | PA14_25790 | 37749 | |
| PA2968 | PA14_25650 | 47840 | fabD |
| PA2969 | PA14_25640 | 28412 | plsX |
| PA2970 | PA14_25630 | 40582 | rpmF |
| PA3012 | PA14_25100 | 41384 | |
| PA3027 | PA14_24920 | 31944 | |
| PA3081 | PA14_24300 | 54905 | |
| PA3095 | PA14_24100 | 41602 | xcpZ |
| PA3098 | PA14_24060 | 39963 | xcpW |
| PA3118 | PA14_23790 | 31800 | leuB |
| PA3179 | PA14_23110 | 41779 | |
| PA3233 | PA14_22370 | 24302‡ | |
| PA3238 | PA14_22310 | 55432‡ | |
| PA3247 | PA14_21990 | 28575‡ | |
| PA3248 | PA14_21980 | 25759 | |
| PA3268 | PA14_21730 | 47846‡ | |
| PA3345 | PA14_20800 | 27890‡ | |
| PA3347 | PA14_20770 | 39911 | |
| PA3383 | PA14_20320 | 41513‡ | phnD |
| PA3396 | PA14_20150 | 31782 | nosL |
| PA3418 | PA14_19870 | 25718 | ldh |
| PA3422 | PA14_19810 | 29260 | |
| PA3438 | PA14_19630 | 28606 | folE1 |
| PA3469 | PA14_19210 | 33802‡ | |
| PA3472 | PA14_19170 | 47128 | |
| PA3476 | PA14_19130 | 33961 | rhlI |
| PA3477 | PA14_19120 | 37943 | rhlR |
| PA3525 | PA14_18740 | 46168‡ | argG |
| PA3527 | PA14_18710 | 38380† | pyrC |
| PA3530 | PA14_18680 | 55172‡ | |
| PA3573 | PA14_18090 | 54968 | |
| PA3579 | PA14_18010 | 42737‡ | |
| PA3604 | PA14_17670 | 44732 | |
| PA3613 | PA14_17580 | 53039 | |
| PA3617 | PA14_17530 | 35423 | recA |
| PA3623 | PA14_17470 | 39999 | |
| PA3667 | PA14_16930 | 25721‡ | |
| PA3670 | PA14_16890 | 33497‡ | |
| PA3675 | PA14_16830 | 28289 | |
| PA3690 | PA14_16660 | 28364‡ | |
| PA3725 | PA14_16220 | 41538 | recJ |
| PA3747 | PA14_15940 | 27351 | |
| PA3761 | PA14_15780 | 56500 | |
| PA3766 | PA14_15700 | 33551 | |
| PA3781 | PA14_15180 | 44327‡ | |
| PA3792 | PA14_15030 | 40358‡ | leuA |
| PA3817 | PA14_14690 | 34797‡ | |
| PA3818 | PA14_14680 | 38519† | |
| PA3822 | PA14_14610 | 52713‡ | |
| PA3840 | PA14_14340 | 33029 | |
| PA3844 | PA14_14290 | 24562‡ | |
| PA3863 | PA14_14010 | 26117 | |
| PA3888 | PA14_13610 | 39654 | |
| PA3920 | PA14_13170 | 24602 | |
| PA3929 | PA14_13040 | 31844‡ | cioB |
| PA3949 | PA14_12770 | 33730 | |
| PA3973 | PA14_12440 | 5999‡ | |
| PA3976 | PA14_12400 | 41228 | |
| PA4003 | PA14_12060 | 31916 | pbpA |
| PA4011 | PA14_11960 | 32590 | |
| PA4078 | PA14_11140 | 39678 | |
| PA4081 | PA14_11110 | 41770 | cupB6 |
| PA4094 | PA14_10940 | 39240 | |
| PA4096 | PA14_10910 | 34683 | |
| PA4117 | PA14_10700 | 29909‡ | |
| PA4131 | PA14_10540 | 26848‡ | |
| PA4132 | PA14_10530 | 31809 | |
| PA4133 | PA14_10500 | 40170‡ | ccoN |
| PA4160 | PA14_10160 | 40138 | fepD |
| PA4161 | PA14_10140 | 44757 | fepG |
| PA4171 | PA14_09940 | 32081 | |
| PA4188 | PA14_09730 | 32052‡ | |
| PA4196 | PA14_09690 | 28988 | |
| PA4199 | PA14_09630 | 39827‡ | |
| PA4206 | PA14_09530 | 40815 | mexH |
| PA4207 | PA14_09520 | 43615‡ | mexI |
| PA4219 | PA14_09370 | 46091 | |
| PA4221 | PA14_09340 | 41286 | fptA |
| PA4231 | PA14_09210 | 35443 | pchA |
| PA4236 | PA14_09150 | 29943‡ | katA |
| PA4284 | PA14_55670 | 31955 | recB |
| PA4297 | PA14_55820 | 31903‡ | |
| PA4317 | PA14_56090 | 29512 | |
| PA4324 | PA14_56180 | 27409 | |
| PA4325 | PA14_56190 | 44483 | |
| PA4347 | PA14_56530 | 40158 | |
| PA4394 | PA14_57110 | 36113 | |
| PA4406 | PA14_57260 | 34855 | lpxC |
| PA4423 | PA14_57480 | 41535 | |
| PA4441 | PA14_57690 | 23324 | |
| PA4459 | PA14_57910 | 23553‡ | |
| PA4463 | PA14_57950 | 53888 | |
| PA4476 | PA14_58090 | 30587 | |
| PA4491 | PA14_58270 | 24252‡ | |
| PA4496 | PA14_58350 | 41807‡ | |
| PA4497 | PA14_58360 | 42056 | |
| PA4502 | PA14_58420 | 44163‡ | |
| PA4514 | PA14_58570 | 42033‡ | |
| PA4526 | PA14_58750 | 34455‡ | pilB |
| PA4536 | PA14_58850 | 22523 | |
| PA4541 | PA14_58900 | 28288 | |
| PA4544 | PA14_60210 | 55505 | rluD |
| PA4545 | PA14_60230 | 29198§ | comL |
| PA4547 | PA14_60260 | 37300 | pilR |
| PA4593 | PA14_60780 | 42490 | |
| PA4600 | PA14_60860 | 55219 | nfxB |
| PA4648 | PA14_61500 | 56786 | |
| PA4660 | PA14_61640 | 34312 | phr |
| PA4664 | PA14_61680 | 46240‡ | |
| PA4667 | PA14_61720 | 39262§ | |
| PA4694 | PA14_62130 | 25072‡ | ilvC |
| PA4700 | PA14_62200 | 28179‡ | mrcB |
| PA4704 | PA14_62260 | 36915‡ | ppkA |
| PA4725 | PA14_62530 | 33836* | cbrA |
| PA4728 | PA14_62570 | 52829‡ | folK |
| PA4729 | PA14_62580 | 38628‡ | panB |
| PA4730 | PA14_62590 | 42078‡ | panC |

TABLE 2-continued

List of PA14 mutants exhibiting reduced biofilm formation as compared to the wild-type, determined by microscopic analysis.

| PAO1 ortholog | PA14 gene locus | Mutant-ID | Gene name |
|---|---|---|---|
| PA4733 | PA14_62630 | 32650 | acsB |
| PA4740 | PA14_62710 | 31610* | pnp |
| PA4742 | PA14_62730 | 57118 | truB |
| PA4743 | PA14_62740 | 47467‡ | rbfA |
| PA4745 | PA14_62770 | 55834 | nusA |
| PA4752 | PA14_62870 | 33950 | rrmJ |
| PA4756 | PA14_62910 | 32277 | carB |
| PA4758 | PA14_62930 | 39940‡ | carA |
| PA4763 | PA14_63010 | 32258‡ | recN |
| PA4772 | PA14_63100 | 52887 | |
| PA4781 | PA14_63210 | 55086 | |
| PA4792 | PA14_63330 | 37901§ | |
| PA4852 | PA14_64180 | 33692* | |
| PA4858 | PA14_64270 | 25134‡ | |
| PA4867 | PA14_64370 | 25328 | ureB |
| PA4876 | PA14_64480 | 53454 | osmE |
| PA4901 | PA14_64770 | 30732‡ | mdlC |
| PA4911 | PA14_64880 | 33498 | |
| PA4922 | PA14_65000 | 29273‡ | azu |
| PA4924 | PA14_65030 | 38789 | |
| PA4925 | PA14_65040 | 32057‡ | |
| PA4958 | PA14_65520 | 44040‡ | |
| PA4966 | PA14_65640 | 34730 | |
| PA4970 | PA14_65700 | 31922 | |
| PA4990 | PA14_65990 | 25612 | qacH |
| PA4994 | PA14_66040 | 35943‡ | |
| PA5002 | PA14_66140 | 27910‡ | |
| PA5014 | PA14_66270 | 41433‡ | glnE |
| PA5028 | PA14_66480 | 14051§ | |
| PA5038 | PA14_66600 | 38358‡ | aroB |
| PA5042 | PA14_66640 | 26804 | pilO |
| PA5045 | PA14_66670 | 42024‡ | ponA |
| PA5048 | PA14_66700 | 24281 | |
| PA5083 | PA14_67140 | 48596 | |
| PA5100 | PA14_67350 | 33943‡ | hutU |
| PA5111 | PA14_67500 | 40398 | gloA3 |
| PA5113 | PA14_67520 | 35504 | |
| PA5118 | PA14_67580 | 43832‡ | thiI |
| PA5132 | PA14_67780 | 24033 | |
| PA5134 | PA14_67810 | 26367* | |
| PA5139 | PA14_67860 | 48309 | |
| PA5181 | PA14_68440 | 31534 | |
| PA5192 | PA14_68580 | 52736‡ | pckA |
| PA5197 | PA14_68660 | 40781‡ | rimK |
| PA5198 | PA14_68670 | 6442 | |
| PA5224 | PA14_69000 | 31097‡ | pepP |
| PA5225 | PA14_69010 | 37268‡ | |
| PA5235 | PA14_69130 | 39942‡ | glpT |
| PA5247 | PA14_69280 | 33874 | |
| PA5263 | PA14_69500 | 44940 | argH |
| PA5274 | PA14_69630 | 29539 | rnk |
| PA5296 | PA14_69910 | 41875 | rep |
| PA5306 | PA14_70060 | 29916 | |
| PA5313 | PA14_70160 | 43085‡ | |
| PA5325 | PA14_70300 | 36265 | |
| PA5342 | PA14_70530 | 29156‡ | |
| PA5345 | PA14_70570 | 30900 | recG |
| PA5346 | PA14_70580 | 23658 | |
| PA5350 | PA14_70630 | 47295 | rubA2 |
| PA5353 | PA14_70670 | 31904‡ | glcF |
| PA5360 | PA14_70750 | 48234‡ | phoB |
| PA5368 | PA14_70850 | 32089 | pstC |
| PA5369 | PA14_70860 | 31354 | |
| PA5380 | PA14_71070 | 24457 | |
| PA5398 | PA14_71260 | 48591§ | |
| PA5399 | PA14_71280 | 32077 | |
| PA5414 | PA14_71450 | 33289 | |
| PA5430 | PA14_71670 | 42169 | |
| PA5435 | PA14_71720 | 39663 | |
| PA5440 | PA14_71820 | 29327‡ | |
| PA5443 | PA14_71870 | 41306 | uvrD |
| PA5460 | PA14_72060 | 33760 | |
| PA5476 | PA14_72280 | 31725‡ | citA |
| PA5481 | PA14_72360 | 39315 | |
| PA5487 | PA14_72420 | 33256‡ | |
| PA5493 | PA14_72490 | 31829 | polA |
| PA5508 | PA14_72690 | 41923‡ | |
| PA5547 | PA14_73150 | 35939 | |
| PA5563 | PA14_73350 | 29870 | soj |
| PA5565 | PA14_73370 | 34284*,† | gidA |
| PA5567 | PA14_73400 | 38726‡ | |

*A second mutant with a transposon insertion within the same gene (other mutant-ID) was found in the poor biofilm cluster
†A re-picked mutant with a transposon insertion within the same gene (same mutant-ID) was found in the poor biofilm cluster
‡A second mutant with a transposon insertion within the same gene (other mutant-ID) was found in the wild-type cluster
§A second mutant with a transposon insertion within the same gene (other mutant-ID) was found in the enhanced biofilm cluster

TABLE 3

List of PA14 mutants exhibiting enhanced biofilm formation as compared to the wild-type, determined by microscopic analysis.

| PAO1 ortholog | PA14 gene locus | Mutant-ID | Gene name |
|---|---|---|---|
| | | 39620 | |
| | | 41502 | |
| | | 42199 | |
| | | 43839 | |
| | | 46402 | |
| | | 52817‡ | |
| | | 55688 | |
| | | 56848 | |
| | PA14_00980 | 31194§ | |
| | PA14_03310 | 42475 | |
| | PA14_04010 | 32273‡ | |
| | PA14_10300 | 6864 | |
| | PA14_13900 | 44987 | |
| | PA14_15450 | 47016‡ | merD |
| | PA14_16290 | 46259 | |
| | PA14_20520 | 42087‡ | |
| | PA14_22530 | 42126‡ | |
| | PA14_23360 | 33590 | wzz |
| | PA14_28820 | 55948 | |
| | PA14_31000 | 45275 | |
| | PA14_31270 | 5295‡ | |
| | PA14_33330 | 44537 | |
| | PA14_35840 | 56424 | |
| | PA14_35860 | 53858 | PAGI-1(17) |
| | PA14_49520 | 35764‡ | |
| | PA14_54070 | 5177 | |
| | PA14_55080 | 34816 | |
| | PA14_59150 | 35368 | ssb |
| | PA14_59180 | 36405 | topA |
| | PA14_59900 | 28987 | |
| | PA14_67190 | 45324 | |
| | PA14_69510 | 37382 | |
| PA0006 | PA14_00070 | 26586 | |
| PA0026 | PA14_00300 | 26176‡ | plcB |
| PA0029 | PA14_00340 | 26493 | |
| PA0031 | PA14_00380 | 26100‡ | betC |
| PA0037 | PA14_00460 | 29263 | trpI |
| PA0052 | PA14_00650 | 54390 | |
| PA0066 | PA14_00780 | 30610 | |
| PA0104 | PA14_01270 | 55164‡ | |
| PA0137 | PA14_01680 | 56171 | |
| PA0138 | PA14_01690 | 39216 | |
| PA0161 | PA14_02010 | 52816 | |
| PA0182 | PA14_02300 | 26783 | |
| PA0208 | PA14_02550 | 32272§ | mdcA |
| PA0236 | PA14_02910 | 31642 | |
| PA0291 | PA14_03800 | 35123 | oprE |
| PA0292 | PA14_03810 | 42664 | aguA |
| PA0293 | PA14_03830 | 37497‡ | aguB |

TABLE 3-continued

List of PA14 mutants exhibiting enhanced biofilm formation as compared to the wild-type, determined by microscopic analysis.

| PAO1 ortholog | PA14 gene locus | Mutant-ID | Gene name |
|---|---|---|---|
| PA0303 | PA14_03950 | 56626 | spuG |
| PA0322 | PA14_04210 | 38960‡ | |
| PA0340 | PA14_04440 | 41548‡,§ | |
| PA0347 | PA14_04550 | 56363 | glpQ |
| PA0353 | PA14_04630 | 44579 | ilvD |
| PA0361 | PA14_04730 | 54548‡ | |
| PA0398 | PA14_05210 | 44104 | |
| PA0418 | PA14_05440 | 27114‡ | |
| PA0420 | PA14_05460 | 52689‡ | bioA |
| PA0425 | PA14_05530 | 26977 | mexA |
| PA0430 | PA14_05590 | 39053 | metF |
| PA0450 | PA14_05870 | 38363 | |
| PA0476 | PA14_06230 | 36815 | |
| PA0483 | PA14_06300 | 45164 | |
| PA0503 | PA14_06540 | 56570 | |
| PA0528 | PA14_06880 | 46621 | |
| PA0539 | PA14_07010 | 44284‡ | |
| PA0598 | PA14_07800 | 41514‡ | |
| PA0633 | PA14_08210 | 26940 | |
| PA0779 | PA14_54210 | 39225‡ | |
| PA0842 | PA14_53380 | 22613 | |
| PA0849 | PA14_53290 | 56384‡ | trxB2 |
| PA0899 | PA14_52660 | 32331‡ | aruB |
| PA0933 | PA14_52190 | 25145‡ | ygcA |
| PA0942 | PA14_52070 | 26608 | |
| PA0946 | PA14_52020 | 44752‡ | |
| PA0988 | PA14_51510 | 34744 | |
| PA0993 | PA14_51460 | 45022‡ | cupC2 |
| PA0999 | PA14_51390 | 29310 | pqsD |
| PA1014 | PA14_51220 | 41694‡ | |
| PA1017 | PA14_51170 | 48443 | pauA |
| PA1085 | PA14_50380 | 29986‡,§ | flgJ |
| PA1092 | PA14_50290 | 36424 | fliC |
| PA1093 | PA14_50280 | 26413 | |
| PA1098 | PA14_50200 | 42610‡ | fleS |
| PA1101 | PA14_50140 | 15886‡ | fliF |
| PA1104 | PA14_50100 | 36669* | fliI |
| PA1111 | PA14_50020 | 39352 | |
| PA1113 | PA14_49970 | 41439‡ | |
| PA1121 | PA14_49880 | 57032‡ | |
| PA1138 | PA14_49680 | 35012‡ | |
| PA1145 | PA14_49590 | 31786 | |
| PA1157 | PA14_49440 | 26191‡ | |
| PA1168 | PA14_49310 | 45493 | |
| PA1177 | PA14_49210 | 32282 | napE |
| PA1252 | PA14_48020 | 43118 | |
| PA1257 | PA14_47950 | 56791 | |
| PA1284 | PA14_47600 | 53800‡ | |
| PA1299 | PA14_47410 | 45434 | |
| PA1316 | PA14_47230 | 6577§ | |
| PA1320 | PA14_47160 | 35050 | cyoD |
| PA1374 | PA14_46480 | 26112 | |
| PA1395 | PA14_46380 | 32463 | |
| PA1411 | PA14_46200 | 26734‡ | |
| PA1443 | PA14_45800 | 37315 | fliM |
| PA1446 | PA14_45770 | 31402 | fliP |
| PA1447 | PA14_45760 | 46407‡ | fliQ |
| PA1452 | PA14_45680 | 39335‡ | flhA |
| PA1459 | PA14_45580 | 35248 | |
| PA1468 | PA14_45450 | 35713 | |
| PA1502 | PA14_45000 | 39044 | gcl |
| PA1523 | PA14_44740 | 26789‡ | xdhB |
| PA1544 | PA14_44490 | 26855 | anr |
| PA1580 | PA14_44070 | 34537 | gltA |
| PA1604 | PA14_43760 | 6758‡ | |
| PA1625 | PA14_43510 | 45237 | |
| PA1647 | PA14_43200 | 34890 | |
| PA1658 | PA14_43030 | 54422 | |
| PA1669 | PA14_42900 | 43643‡ | |
| PA1693 | PA14_42620 | 26713 | pscR |
| PA1708 | PA14_42450 | 34677 | popB |
| PA1709 | PA14_42440 | 41685 | popD |
| PA1726 | PA14_42230 | 5084*,‡ | bglX |
| PA1734 | PA14_42120 | 40415 | |
| PA1757 | PA14_41830 | 5955‡ | thrH |
| PA1771 | PA14_41650 | 56371 | |
| PA1799 | PA14_41260 | 55775‡ | |
| PA1856 | PA14_40510 | 55284‡ | ccoN-2 |
| PA1885 | PA14_40130 | 36122 | |
| PA1907 | PA14_39860 | 6781‡ | |
| PA1908 | PA14_39850 | 31431‡ | |
| PA1913 | PA14_39790 | 26678 | |
| PA1941 | PA14_39440 | 26130‡ | |
| PA1996 | PA14_38700 | 26159 | ppiC1 |
| PA2025 | PA14_38330 | 36123 | gor |
| PA2051 | PA14_37980 | 38071‡ | |
| PA2076 | PA14_37660 | 26650‡ | |
| PA2089 | PA14_37490 | 44631‡ | |
| PA2174 | PA14_36470 | 29436 | |
| PA2237 | PA14_35670 | 38795‡ | |
| PA2297 | PA14_34920 | 26122‡ | |
| PA2353 | PA14_34230 | 35064 | |
| PA2410 | PA14_33530 | 352 | |
| PA2431 | PA14_33190 | 39099‡ | |
| PA2455 | PA14_32860 | 33292‡ | |
| PA2479 | PA14_32580 | 35120 | |
| PA2518 | PA14_32080 | 26053§ | xylX |
| PA2525 | PA14_31920 | 26795‡ | |
| PA2529 | PA14_31850 | 42495‡ | |
| PA2543 | PA14_31680 | 26320‡ | |
| PA2592 | PA14_30570 | 35160 | |
| PA2593 | PA14_30560 | 35208§ | |
| PA2609 | PA14_30360 | 38757‡ | |
| PA2613 | PA14_30320 | 39521‡ | |
| PA2651 | PA14_29820 | 36400 | |
| PA2678 | PA14_29480 | 47595 | |
| PA2707 | PA14_29130 | 35395 | |
| PA2815 | PA14_27730 | 6498‡ | |
| PA2869 | PA14_26980 | 34918 | |
| PA2886 | PA14_26750 | 26421‡ | |
| PA2887 | PA14_26730 | 26562 | |
| PA2894 | PA14_26620 | 35731 | |
| PA2922 | PA14_26260 | 35310 | |
| PA2932 | PA14_26130 | 34963‡ | morB |
| PA2985 | PA14_25470 | 24951‡ | |
| PA2999 | PA14_25280 | 43956‡ | nqrA |
| PA3018 | PA14_25030 | 52725 | |
| PA3036 | PA14_24820 | 30983 | |
| PA3114 | PA14_23840 | 40900‡ | truA |
| PA3127 | PA14_23670 | 25570‡ | |
| PA3176 | PA14_23160 | 39204‡ | gltS |
| PA3195 | PA14_22890 | 45102 | gapA |
| PA3203 | PA14_22770 | 35038 | |
| PA3215 | PA14_22640 | 40385‡ | |
| PA3236 | PA14_22330 | 23394 | |
| PA3243 | PA14_22040 | 39233 | minC |
| PA3260 | PA14_21850 | 55251 | |
| PA3262 | PA14_21820 | 56877‡ | fklB |
| PA3310 | PA14_21210 | 26514‡ | |
| PA3317 | PA14_21130 | 34616‡ | |
| PA3337 | PA14_20890 | 29811‡ | rfaD |
| PA3344 | PA14_20810 | 44622 | recQ |
| PA3357 | PA14_20650 | 44591 | dsdA |
| PA3391 | PA14_20230 | 48720 | nosR |
| PA3395 | PA14_20170 | 55106 | nosY |
| PA3409 | PA14_20000 | 30370 | |
| PA3423 | PA14_19800 | 54299‡ | |
| PA3429 | PA14_19710 | 35397 | |
| PA3436 | PA14_19650 | 29168 | |
| PA3452 | PA14_19470 | 44967‡ | mqoA |
| PA3454 | PA14_19430 | 45368 | |
| PA3515 | PA14_18860 | 44571 | |
| PA3516 | PA14_18850 | 37633 | |
| PA3519 | PA14_18810 | 41243‡ | |
| PA3545 | PA14_18500 | 45025‡ | algG |
| PA3548 | PA14_18450 | 26301‡ | algI |
| PA3580 | PA14_17990 | 5164 | |
| PA3593 | PA14_17810 | 26812‡ | |

TABLE 3-continued

List of PA14 mutants exhibiting enhanced biofilm formation as compared to the wild-type, determined by microscopic analysis.

| PAO1 ortholog | PA14 gene locus | Mutant-ID | Gene name |
|---|---|---|---|
| PA3596 | PA14_17760 | 32336 | |
| PA3606 | PA14_17650 | 41654 | |
| PA3615 | PA14_17550 | 34821 | |
| PA3659 | PA14_17030 | 40944‡ | |
| PA3663 | PA14_16980 | 57114 | |
| PA3676 | PA14_16820 | 39331‡ | |
| PA3705 | PA14_16460 | 4849 | |
| PA3713 | PA14_16360 | 31434 | |
| PA3728 | PA14_16190 | 37614‡ | |
| PA3793 | PA14_15020 | 37337 | |
| PA3882 | PA14_13690 | 40495 | |
| PA3902 | PA14_13420 | 38166 | |
| PA3921 | PA14_13150 | 36060‡ | |
| PA3975 | PA14_12410 | 41942‡ | |
| PA3980 | PA14_12350 | 31329 | |
| PA3981 | PA14_12330 | 45445 | |
| PA4070 | PA14_11240 | 24061* | |
| PA4079 | PA14_11130 | 45257 | |
| PA4166 | PA14_09990 | 56522 | |
| PA4197 | PA14_09680 | 45377‡ | |
| PA4202 | PA14_09580 | 32302 | |
| PA4208 | PA14_09500 | 45413 | opmD |
| PA4315 | PA14_56070 | 34492 | mvaT |
| PA4320 | PA14_56130 | 41647‡ | |
| PA4333 | PA14_56300 | 35583‡ | |
| PA4343 | PA14_56470 | 30635‡ | |
| PA4355 | PA14_56640 | 15016‡ | |
| PA4383 | PA14_56980 | 55891 | |
| PA4437 | PA14_57640 | 54111‡ | |
| PA4447 | PA14_57770 | 26315‡ | hisC1 |
| PA4448 | PA14_57780 | 29380‡ | hisD |
| PA4490 | PA14_58260 | 34952 | |
| PA4495 | PA14_58330 | 45330 | |
| PA4522 | PA14_58670 | 43134 | ampD |
| PA4523 | PA14_58690 | 44567‡ | |
| PA4545 | PA14_60230 | 31776§ | comL |
| PA4589 | PA14_60730 | 30743‡ | |
| PA4617 | PA14_61090 | 35099 | |
| PA4627 | PA14_61220 | 37746‡ | |
| PA4640 | PA14_61400 | 39630 | mqo |
| PA4653 | PA14_61550 | 38888 | |
| PA4654 | PA14_61560 | 56527‡ | |
| PA4667 | PA14_61720 | 24349§ | |
| PA4705 | PA14_62270 | 45224 | |
| PA4706 | PA14_62280 | 39440 | |
| PA4735 | PA14_62650 | 40449‡ | |
| PA4785 | PA14_63250 | 34726‡ | |
| PA4789 | PA14_63300 | 48573 | |
| PA4792 | PA14_63330 | 44909§ | |
| PA4869 | PA14_64400 | 28079‡ | |
| PA4907 | PA14_64840 | 34639 | |
| PA4915 | PA14_64920 | 30889 | |
| PA4917 | PA14_64940 | 54555 | |
| PA4968 | PA14_65670 | 54519‡ | |
| PA4984 | PA14_65900 | 56513 | |
| PA4995 | PA14_66050 | 35246 | |
| PA5015 | PA14_66290 | 39618 | aceA |
| PA5028 | PA14_66480 | 45179§ | |
| PA5089 | PA14_67220 | 45137 | |
| PA5096 | PA14_67300 | 31659‡ | |
| PA5098 | PA14_67320 | 44624 | hutH |
| PA5136 | PA14_67830 | 45645 | |
| PA5137 | PA14_67840 | 39024 | |
| PA5210 | PA14_68820 | 39336 | |
| PA5215 | PA14_68870 | 29888 | gcvT1 |
| PA5227 | PA14_69030 | 38792 | |
| PA5239 | PA14_69190 | 34208‡ | rho |
| PA5256 | PA14_69400 | 57151 | dsbH |
| PA5291 | PA14_69850 | 27066 | |
| PA5307 | PA14_70070 | 45113 | |
| PA5330 | PA14_70360 | 43003‡ | |
| PA5340 | PA14_70490 | 56665 | |
| PA5363 | PA14_70780 | 32407 | |
| PA5370 | PA14_70920 | 55507 | |
| PA5384 | PA14_71110 | 39582 | |
| PA5385 | PA14_71120 | 27032 | |
| PA5398 | PA14_71260 | 38249§ | |
| PA5450 | PA14_71940 | 45670‡ | wzt |
| PA5451 | PA14_71960 | 45203 | wzm |
| PA5454 | PA14_72000 | 52924‡ | rmd |
| PA5455 | PA14_72010 | 32193‡ | |
| PA5472 | PA14_72220 | 46334 | |
| PA5479 | PA14_72340 | 28970‡ | gltP |
| PA5488 | PA14_72430 | 35339‡ | |
| PA5544 | PA14_73110 | 36447 | |
| PA5550 | PA14_73190 | 35650‡ | glmR |
| PA5551 | PA14_73200 | 15036 | |
| PA5558 | PA14_73290 | 47381 | atpF |

*A second mutant with a transposon insertion within the same gene (other mutant-ID) was found in the enhanced biofilm cluster
†A re-picked mutant with a transposon insertion within the same gene (same mutant-ID) was found in the enhanced biofilm cluster
‡A second mutant with a transposon insertion within the same gene (other mutant-ID) was found in the wild-type cluster
§A second mutant with a transposon insertion within the same gene (other mutant-ID) was found in the poor biofilm cluster

BRIEF DESCRIPTION OF THE FIGURES

FIG. 9 3D visualization of representative PA14 biofilms of the internal controls: (a) poor biofilm (pqsA mutant), (b) normal biofilm (wild-type) and (c) enhanced biofilm (flgF mutant) after 72 h of incubation. Bars, 150 mm.

FIG. 10 2D projection of the distribution of the whole transposon mutant library. Cluster boundaries are shown by black lines; mutants and internal controls are coloured as indicated.

Figure 1:
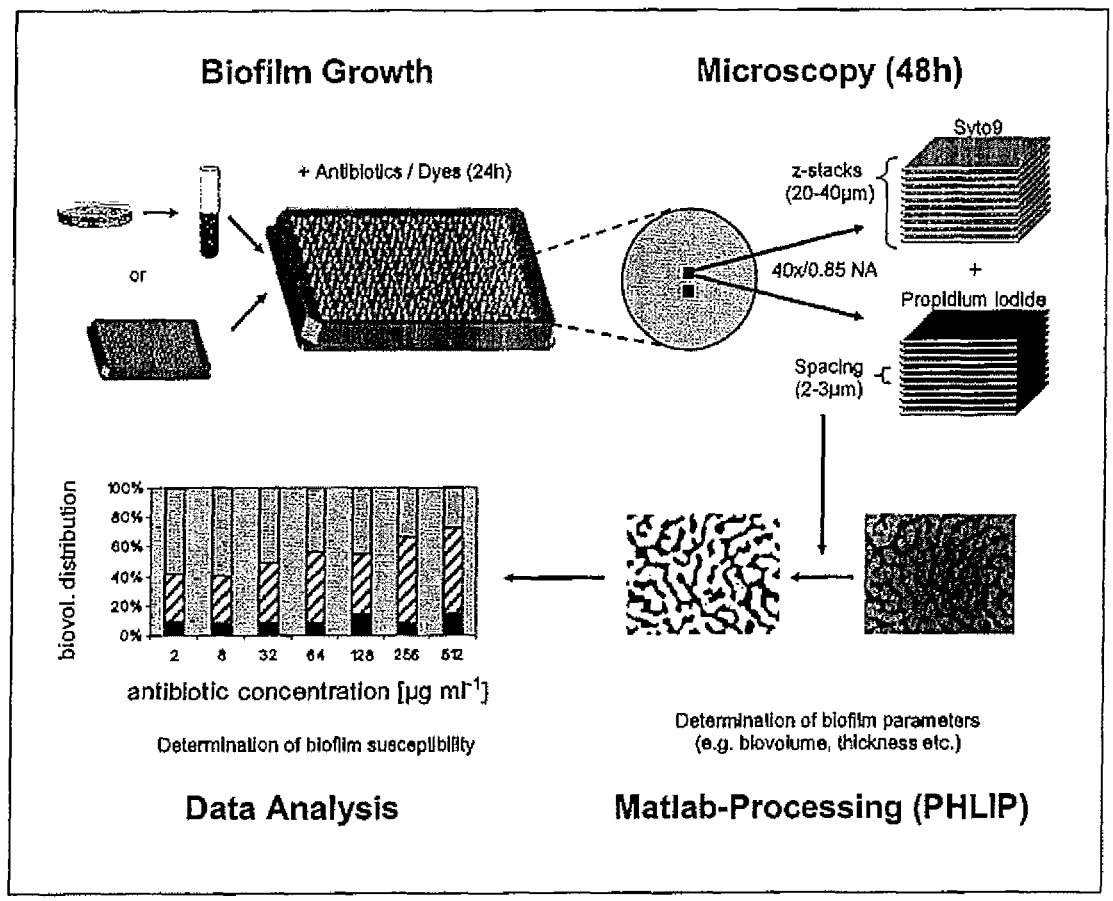
FIG. 1 Workflow of the biofilm susceptibility testing system.
Figure 2:
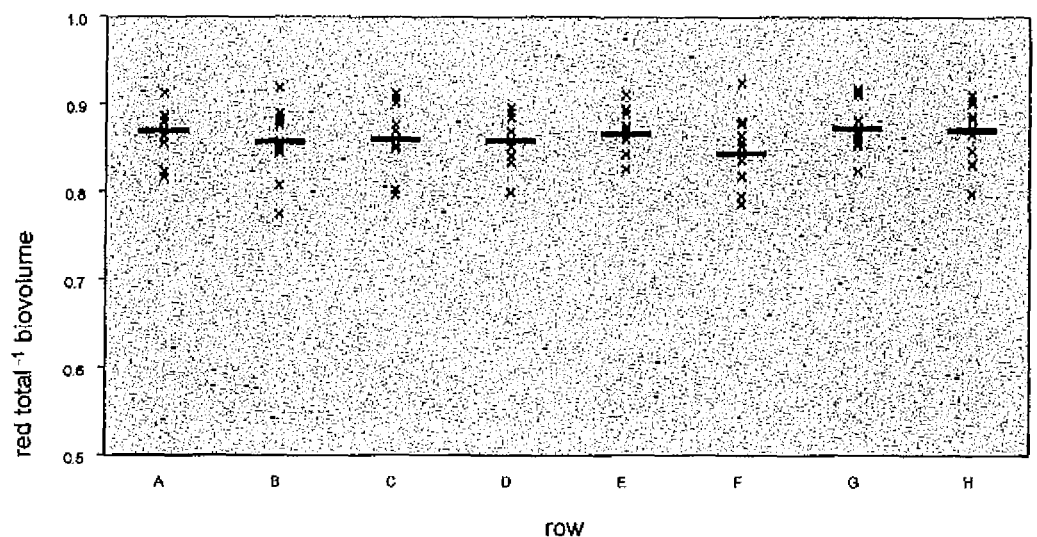
FIG. 2 Robustness of the PHLIP-calculated biofilm parameters. Red versus total biovolume ratio of PA14 replicates grown in a 96-well plate plotted row-wise. Mean values of the rows are represented as bars.
Figure 3:
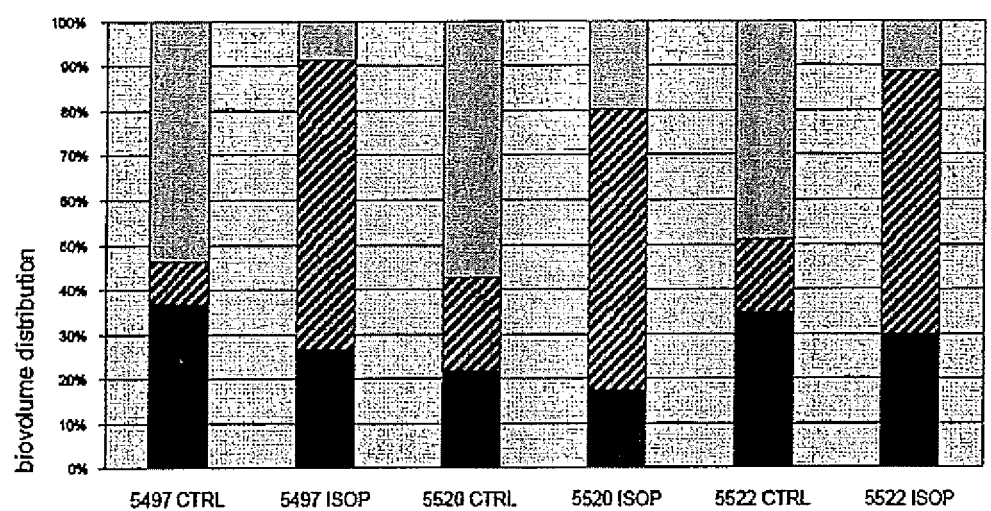
FIG. 3 Isopropanol treatment of biofilms as killing control. Processed 3D visualizations (Easy 3D projection) of untreated (CTRL) and isopropanol-treated (ISOP) biofilms (Syto9=blue, PI=yellow, overlap=white). Distribution of PI-stained (dark), colocalized (hatched) and Syto9-stained (light) biovolume of three clinical strains (5497, 5520 and 5522). Biovolume data are mean values of four independent replicates. The overall s.d. values for the green, co-localized and red fractions for each strain are: 5497, 8.7%/1.0%/9.2%; 5520, 0.4%/7.1%/2.5%; and 5522, 4.9%/4.5%/5.3%.
Figure 4:
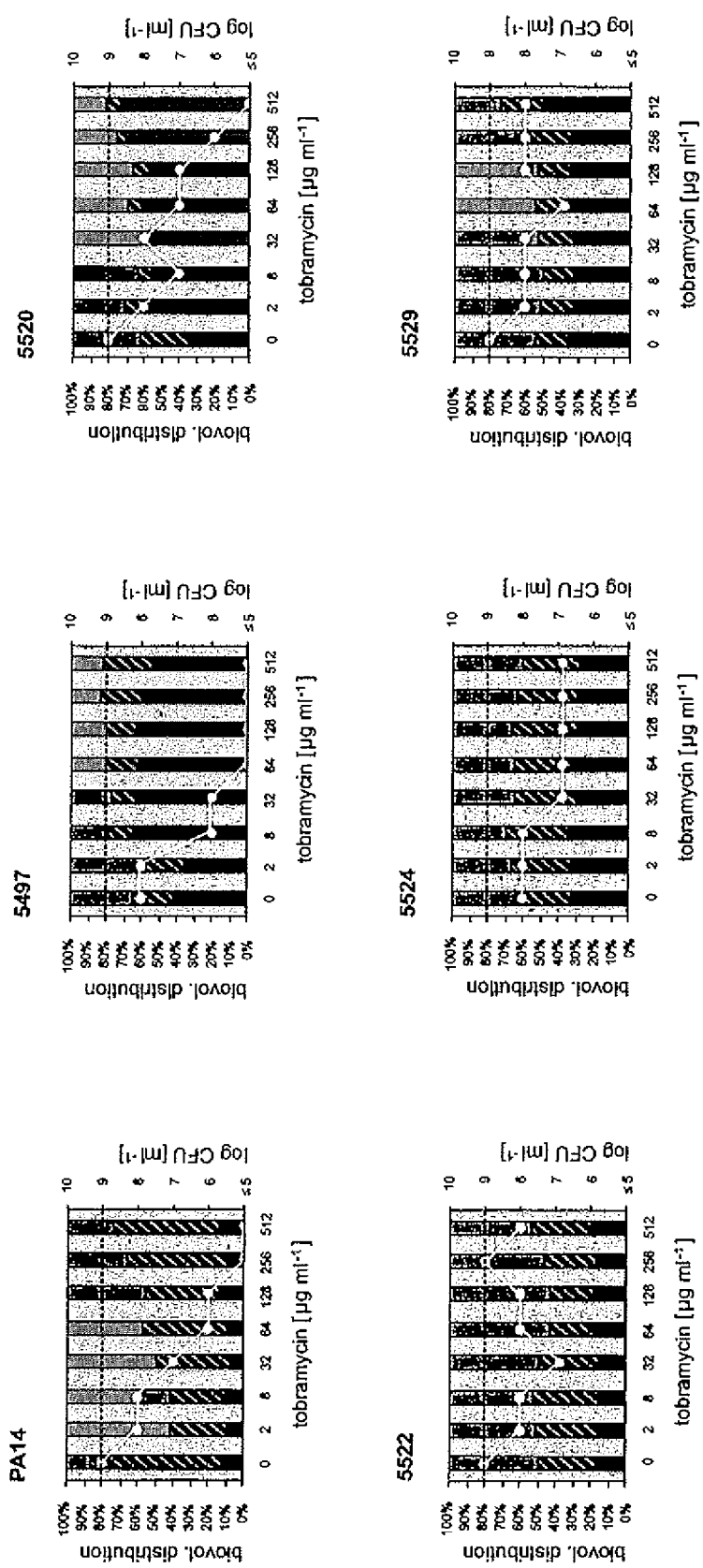
FIG. 4 Responsiveness of tobramycin-treated biofilms. Distribution of the PI-stained (dark), colocalized (hatched) and Syto9-stained (light) biovolumes as well as CFU counts (solid white line) from PA14 and five clinical strains exposed to increasing concentrations of tobramycin. The black dotted line marks the 80% threshold of PI (and colocalized) fluorescence. Biovolume data are mean values of three independent replicates. The overall s.d. values for the green, colocalized and red fractions are as follows: PA14, 7.9%; 6.5%; 4.5%; 5497, 4.3%/2.6%/5.6%; 5520, 5.8%/2.9%/6.8%; 5522, 2.8%/3.7%/2.0%; 5524, 4.9%/2.5%/3.8%; and 5529, 5.2%/3.8%/3.8%.
Figure 5:
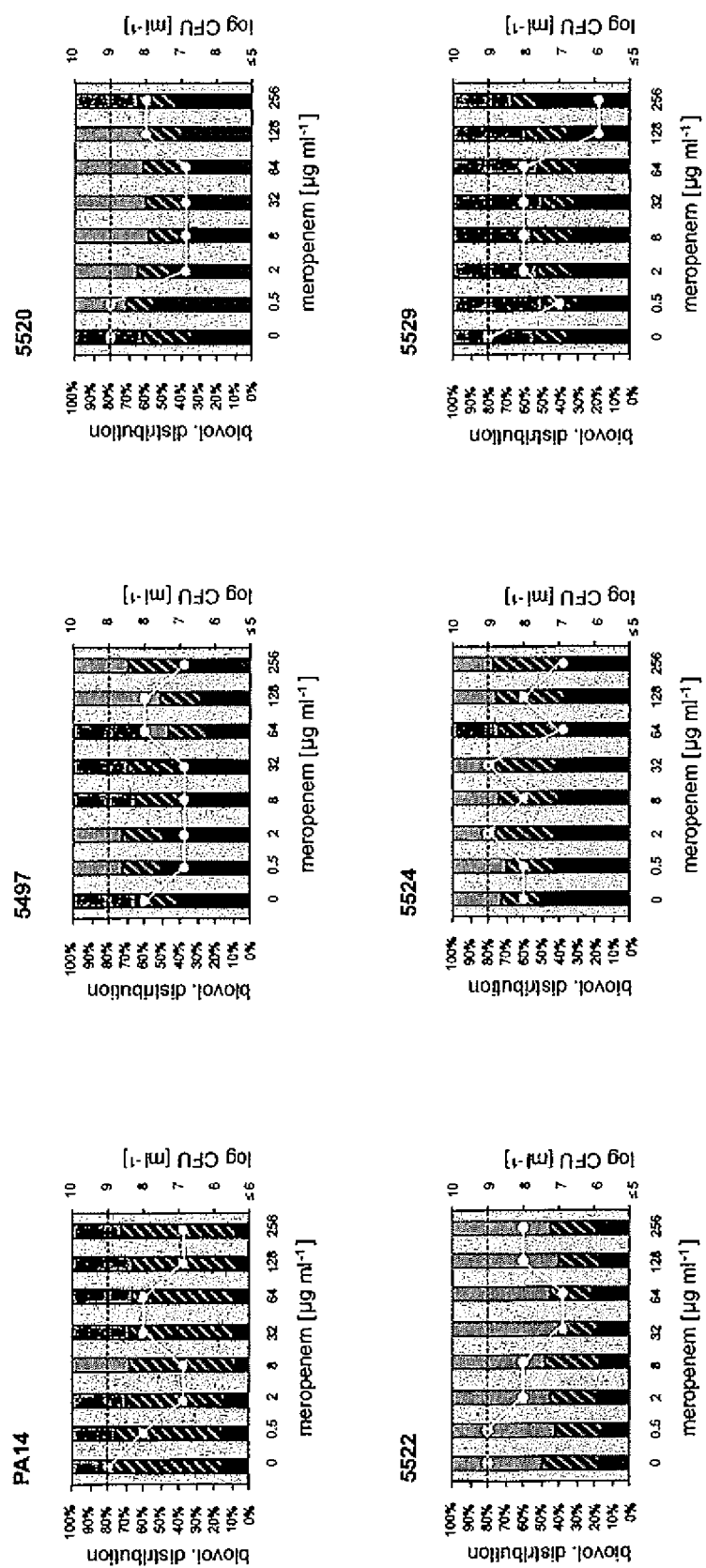
FIG. 5 | Responsiveness of the meropenem-treated biofilms. Distribution of the PI stained (dark), the co-localized (hatched) and the Syto9 stained (light) biovolume and CFU counts (solid white line) of PA14 and 5 clinical strains exposed to increasing concentrations of meropenem. The black dotted line marks the 80% threshold of PI (and co-localized) fluorescence. Biovolume data are mean values of three independent replicates. The overall SD for the green, the co-localized and the red fraction are: PA14 (4.5%/4.9%/3.9%), 5497 (6.6%/3.0%/6.7%), 5520 (4.4%/3.4%/5.3%), 5522 (4.0%/4.0%/3.5%), 5524 (4.0%/3.7%/4.6%) and 5529 (4.8%/2.7%/4.4%).
Figure 6:
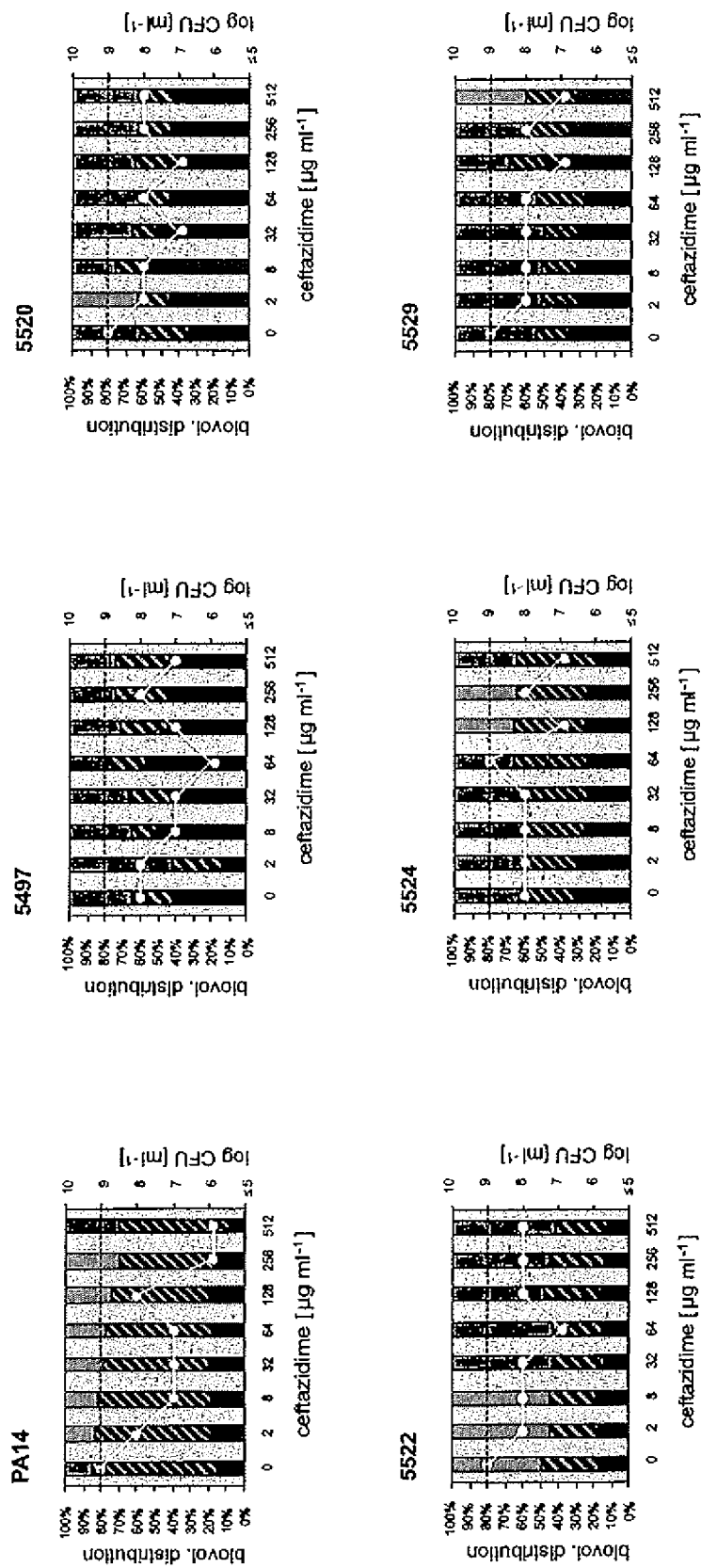
FIG. 6 | Responsiveness of the ceftazidime-treated biofilms. Distribution of the PI stained (dark), the co-localized (hatched) and the Syto9 stained (light) biovolume and CFU counts (solid white line) of PA 14 and 5 clinical strains exposed to increasing concentrations of ceftazidime. The black dotted line marks the 80% threshold of PI (and co-localized) fluorescence. Biovolume data are mean values of three independent replicates. The overall SD for the green, the co-localized and the red fraction are: PA14 (3.5%/4.0%/2.2%), 5497 (6.2%/3.4%/7.4%), 5520 (5.5%/3.0%/7.0%), 5522 (2.7%/3.4%/2.3%), 5524 (6.5%/3.0%/5.3%) and 5529 (6.1%/3.1%/5.9%).
Figure 7:
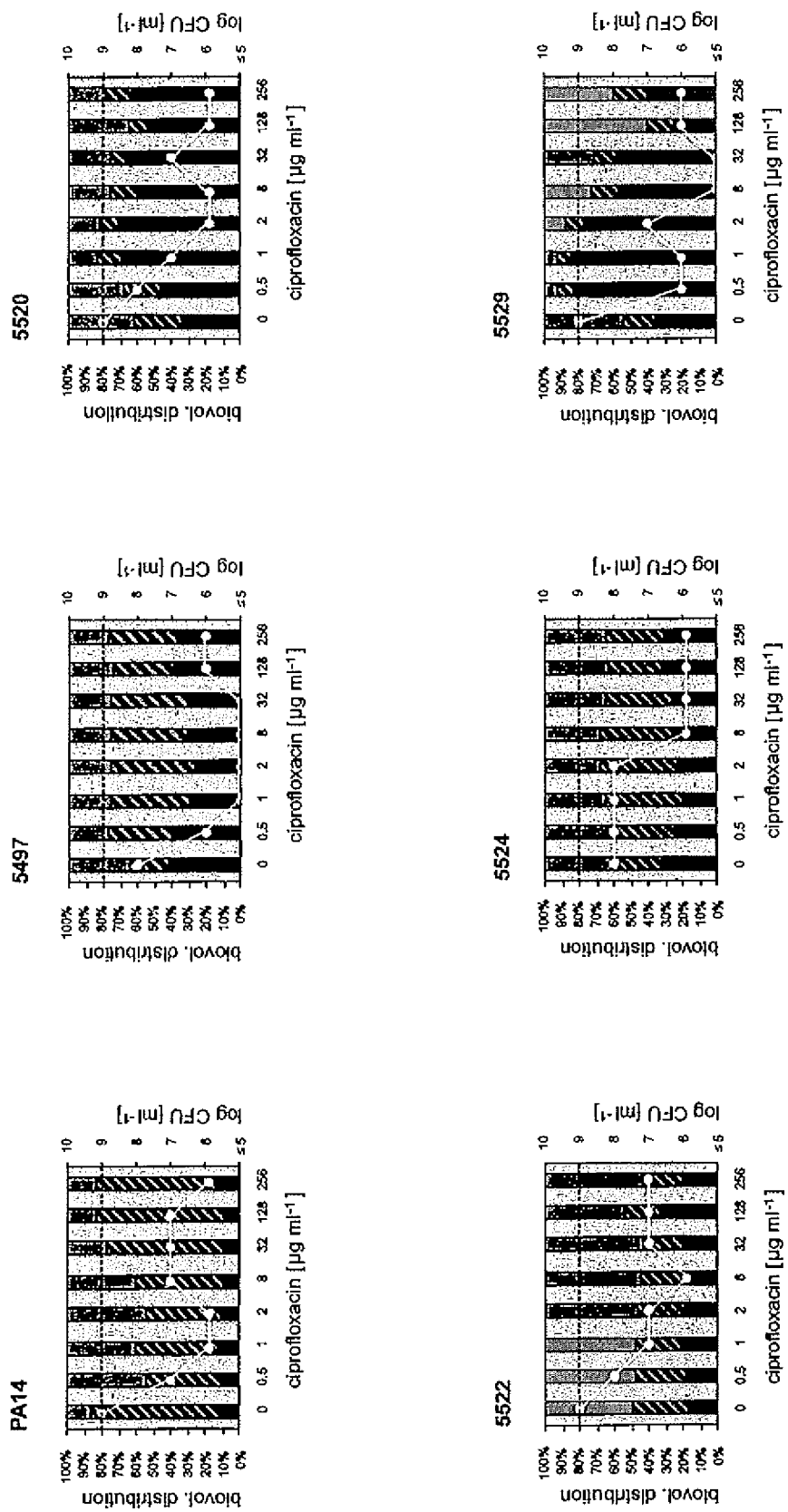
FIG. 7 | Responsiveness of the ciprofloxacin-treated biofilms. Distribution of the PI stained (dark), the co-localized (hatched) and the Syto9 stained (light) biovolume and CFU counts (solid white line) of PA14 and 5 clinical strains exposed to increasing concentrations of ciprofloxacin. The black dotted line marks the 80% threshold of PI (and co-localized) fluorescence. Biovolume data are mean values of three independent replicates. The overall SD for the green, the co-localized and the red fraction are: PA14 (4.3%/3.5%/2.5%), 5497 (2.4%/4.7%/5.6%), 5520 (6.3%/3.4%/7.2%), 5522 (4.6%/3.9%/4.0%), 5524 (7.1%/4.0%/5.0%) and 5529 (4.9%/3.2%/6.9%).
Figure 8:
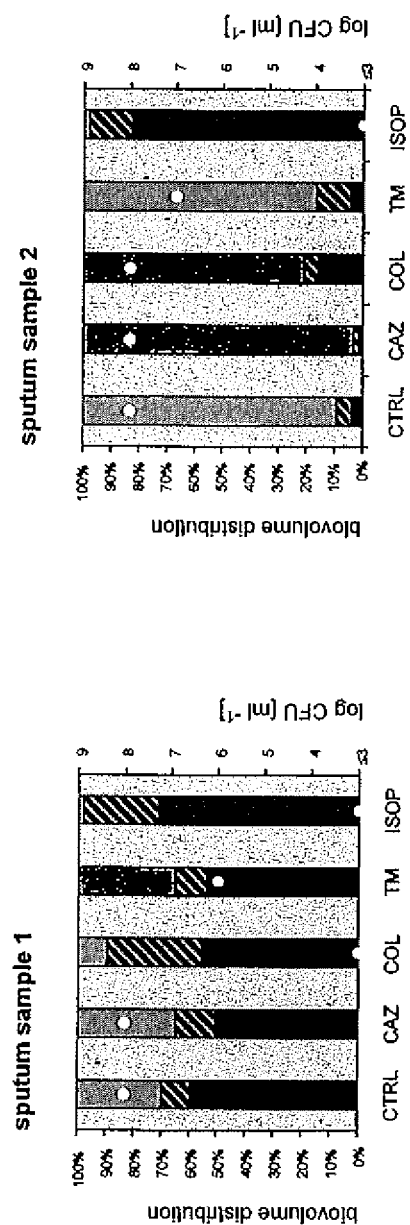
FIG. 8 Application of biofilm susceptibility testing to two sputum samples. (a) Processed 3D visualizations (Easy 3D projection) of biofilms of two sputum samples treated with isopropanol and the antibiotics tobramycin, ceftazidime and colistin (1 mg ml$^{-1}$). (b) Distribution of the PI-stained (dark), colocalized (hatched) and Syto9-stained (light) biovolume and CFU counts (white dots) of the two sputum samples. Biovolume data are mean values of three independent replicates. The overall s.d. values for the green, colocalized and red fractions are as follows: sputum sample 1, 5.5%/3.3%/8.5%; and sputum sample 2, 2.6%/2.3%/1.1%.
Figure 9:
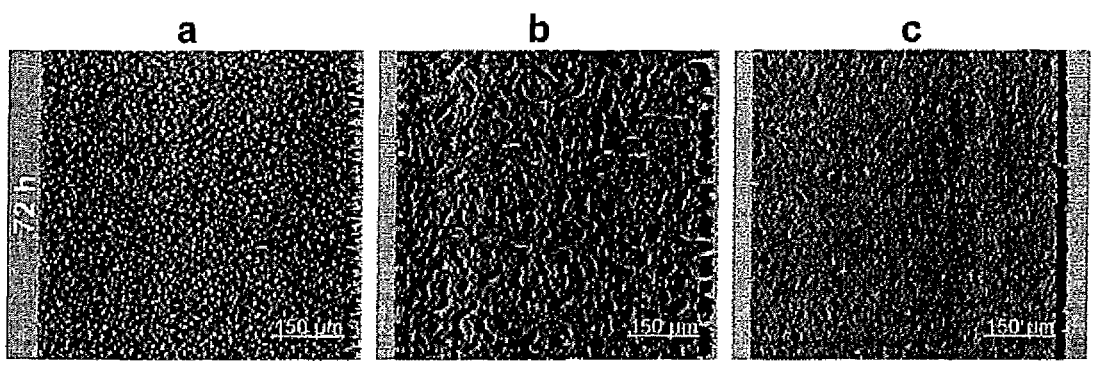
Figure 10:
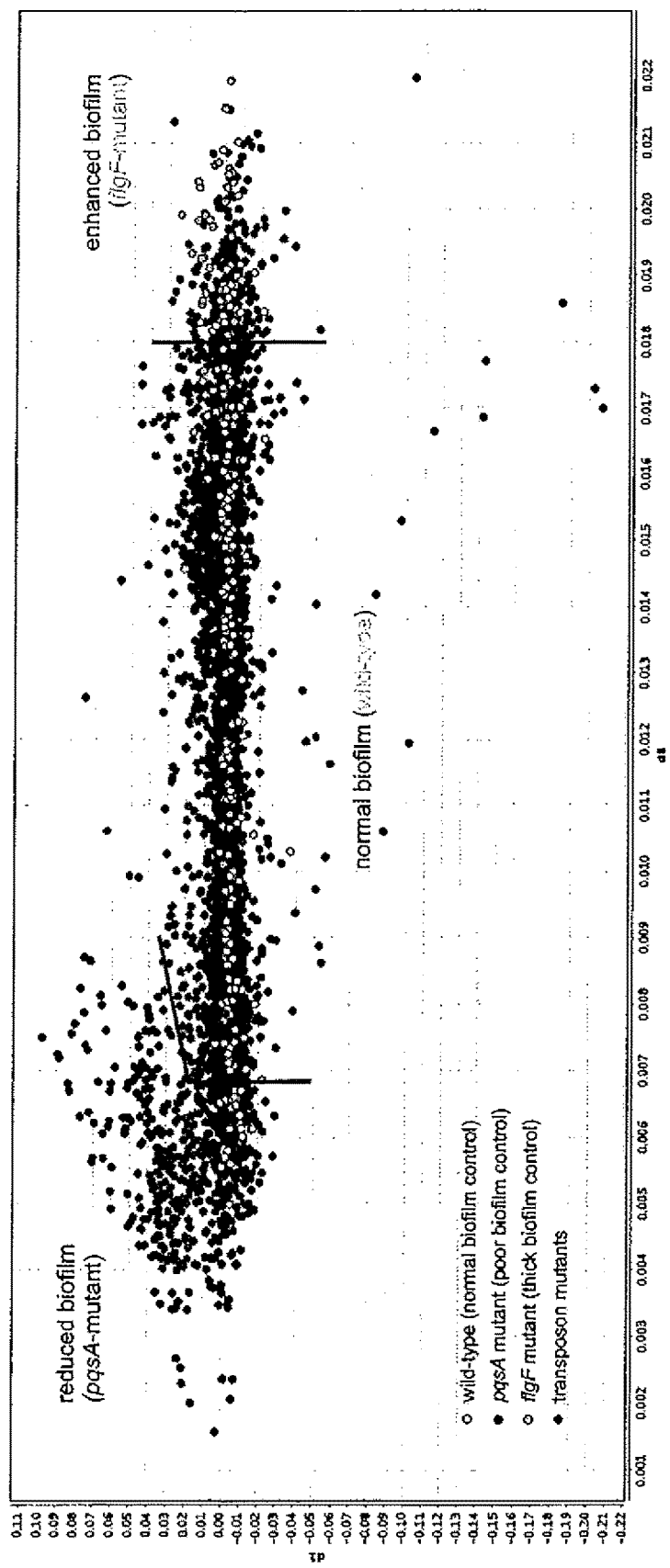

The invention claimed is:

1. A method for screening bacteria on their susceptibility against candidate compounds comprising the steps of:
   a) forming of a biofilm of bacteria on a planar support whereby said planar support is adapted for microscopy;
   b) incubating the formed biofilm of step a) with one or more candidate compounds to be tested;
   c) staining the biofilm of step b) with at least one marker which allows detection of said bacteria and differentiating between live bacteria and dead bacteria;
   d) evaluating an effect of the candidate compounds on bacteria present in the biofilm based on the staining pattern using a microscope to determine the proportions of live bacteria and dead bacteria;
   e) determining susceptibility of the bacteria against the candidate compounds based on the staining pattern of the bacteria, wherein the bacteria are considered to be susceptible to a candidate compound when the proportion of dead bacteria is at least 80%,
      wherein the biofilm of said bacteria is formed in said forming step by cultivating the bacteria on said planar support to allow biofilm formation without continuous fluid flow and without shaking,
      wherein cultivation takes place during said forming step in a rich cultivation medium and cultivation is effected in containers covered with an air-permeable cover foil to prevent formation of an oxygen gradient from an outer to an inner zone of said container covered with said air-permeable cover foil, and
      wherein the cover foil allows a gaseous exchange substantially over the whole area of the cover foil.

2. The method according to claim 1 wherein steps a) through e) screen for antibiotic efficacy of the candidate compounds, and wherein said determining step e) is used to determine whether one or more of the candidate compounds functions as an antimicrobial.

3. The method according to claim 1 wherein formation of the biofilm of bacteria is performed in a well plate.

4. The method according to claim 3 wherein said well plate is selected from the group consisting of a 96 well plate and a 384 well.

5. The method according to claim 1 wherein the evaluating step is effected by using confocal laser scanning microscopy.

6. The method according to claim 1 wherein steps a) through e) are performed repeatedly for different candidate compounds of said one or more candidate compounds for high throughput screening of the candidate compounds.

7. The method according to claim 1 wherein said evaluating step and said determining step both include comparison with a reference sample not incubated with the candidate compounds.

8. The method of claim 1, wherein said staining step is performed with two markers.

9. A method for screening bacteria on their susceptibility against candidate compounds comprising the steps of:
   a) cultivating the bacteria in a rich cultivation medium on a planar support without continuous fluid flow and without shaking to form a biofilm of bacteria on said planar support whereby said planar support is adapted for microscopy, wherein cultivation is effected in containers covered with an air-permeable cover foil to prevent formation of an oxygen gradient from an outer to an inner zone of said container covered with said air-permeable cover foil and wherein the cover foil allows a gaseous exchange substantially over the whole area of the cover foil;
   b) incubating the formed biofilm of step a) with one or more candidate compounds to be tested;
   c) staining the biofilm of step b) with at least one marker which allows detection of said bacteria and allows for differentiating between live bacteria and dead bacteria;
   d) evaluating an effect of the candidate compounds on bacteria present in the biofilm based on the staining pattern of live bacteria and dead bacteria using a microscope to identify and enumerate the live bacteria and dead bacteria;
   e) calculating the percentages of the live bacteria and dead bacteria present in the biofilm; and
   f) determining susceptibility of the bacteria against the candidate compounds based on the staining pattern of the bacteria wherein the bacteria are considered to be susceptible to a candidate compound when the proportion of dead bacteria is at least 80%.

10. The method of claim 9, wherein said staining step is performed with two markers.

* * * * *